US011477736B1

(12) United States Patent
Sivakumaran et al.

(10) Patent No.: US 11,477,736 B1
(45) Date of Patent: Oct. 18, 2022

(54) WEARABLE DEVICE BATTERY CONSERVATION

(71) Applicant: Amazon Technologies, Inc., Seattle, WA (US)

(72) Inventors: Arun Prasath Sivakumaran, Issaquah, WA (US); Ravikant Cherukuri, Redmond, WA (US); Rong Shen, Redmond, WA (US); Amol Vengurlekar, Redmond, WA (US); Sonal Saha, Bellevue, WA (US)

(73) Assignee: Amazon Technologies, Inc., Seattle, WA (US)

( * ) Notice: Subject to any disclaimer, the term of this patent is extended or adjusted under 35 U.S.C. 154(b) by 186 days.

(21) Appl. No.: 16/894,516

(22) Filed: Jun. 5, 2020

(51) Int. Cl.
*H04W 52/02* (2009.01)
*G16H 40/67* (2018.01)
*G06F 1/08* (2006.01)

(52) U.S. Cl.
CPC .......... *H04W 52/0251* (2013.01); *G06F 1/08* (2013.01); *G16H 40/67* (2018.01)

(58) Field of Classification Search
CPC ....... A61B 5/1118; A61B 5/48; A61B 5/0002; A61B 5/0008; A61B 5/0004; A61B 5/6802; A61B 5/411; A61B 5/02438; A61B 5/112; A61B 5/4806; A61B 5/01; A61B 5/0022; A61B 5/14542; A61B 5/1112; A61B 5/6801; A61B 5/1453; A61B 5/6828; A61B 5/0006; A61B 5/6824; A61B 5/6814; A61B 5/6823; A61B 5/6822; G06F 1/08; G06F 1/3296; G16H 40/67; G01K 13/20
See application file for complete search history.

(56) References Cited

U.S. PATENT DOCUMENTS

2012/0316471 A1* 12/2012 Rahman ................ A61B 5/1118
600/595
2015/0237461 A1* 8/2015 Goyal ..................... H04M 1/02
455/41.2
(Continued)

OTHER PUBLICATIONS

Anguelov, D., Srinivasan, P., Koller, D., Thrun, S., Rodgers, J. and Davis, J., "SCAPE: Shape Completion and Animation of People," ACM Trans. Graph. (Proc. SIGGRAPH), 24(3):408-416, Jul. 2005, 9 pages, http://robots.stanford.edu/papers/anguelov.shapecomp.pdf.
(Continued)

*Primary Examiner* — Oussama Roudani
(74) *Attorney, Agent, or Firm* — Athorus, PLLC

(57) ABSTRACT

Described are apparatus, systems, and methods that are operable to conserve battery power of a wearable device by monitoring a state of the user wearing the wearable device and adjusting power state of one or more components of the device based on the determined user state and/or altering a wireless transmission of sensor data collected by the wearable device from the wearable device to a portable device associated with the user. For example, if it is determined that the user is in a sleep state, the wireless connection between the wearable device and the portable device may be terminated, the wireless transmitter and the processor transitioned to a low power state, and sensor data stored in a buffer memory of the wearable device until a defined period of time before the user exits the sleep state and/or upon satisfaction of a buffer usage threshold.

22 Claims, 13 Drawing Sheets

(56) References Cited

U.S. PATENT DOCUMENTS

| | | | | |
|---|---|---|---|---|
| 2016/0058366 | A1* | 3/2016 | Choi | A61B 5/4806 600/595 |
| 2017/0372616 | A1* | 12/2017 | Del Vecchio | G06Q 10/109 |
| 2019/0076066 | A1* | 3/2019 | Ajemba | G16H 50/70 |

OTHER PUBLICATIONS

Balan, A. O. and Black, M. J., "The Naked Truth: Estimating Body Shape under Clothing," In European Conference on Computer Vision (ECCV), 2008, 15 pages, https://www.researchgate.net/profile/Michael_Black6/publication/221305001_The_Naked_Truth_Estimating_Body_Shape_Under_Clothing/links/0fcfd512d21f538458000000/The-Naked-Truth-Estimating-Body-Shape-Under-Clothing.pdf?origin=publication_detail.

Bălan, A. O., Sigal, L., Black, M. J., Davis, J. E. and Haussecker, H. W., "Detailed Human Shape and Pose from Images," In IEEE Conference on Computer Vision and Pattern Recognition (CVPR), 2007, 9 pages.

Bogo, F., Kanazawa, A., Lassner, C., Gehler, P., Romero, J. and Black, M. J., "Keep it SMPL: Automatic Estimation of 3D Human Pose and Shape from a Single Image," In European Conference on Computer Vision (ECCV) 2016, 21 pages, https://arxiv.org/pdf/1607.08128v1.pdf.

Boisvert, J., Shu, C., Wuhrer, S., and Xi, P., "Three-Dimensional Human Shape Inference from Silhouettes: Reconstruction and Validation," Machine Vision and Applications, 24(1):145-157, 2013, 13 pages, http://people.scs.carleton.ca/~c_shu/Publications/silhouettes_human_rec_MVA11.pdf.

Chen, X., Guo, Y., Zhou, B. and Zhao, Q., "Deformable Model for Estimating Clothing and Naked Human Shapes from a Single Image," The Visual Computer, 29(11):1187-1196, 2013, 10 pages.

Chen, Y., Kim, T.-K. and Cipolla, R., "Inferring 3D Shapes and Deformations from Single Views," In European Conference on Computer Vision, 2010, 14 pages.

Chen, Y., Kim, T.-K. and Cipolla, R., Silhouette-Based Object Phenotype Recognition Using 3D Shape Priors. In Inter-national Conference on Computer Vision (ICCV), 2011, 8 pages.

Devries, T. and Taylor, G. W., Learning Confidence for Out-of-Distribution Detection in Neural Networks, arXiv preprint arXiv:1802.04865, 2018, 12 pages.

Dibra, E., Jain, H., Öztireli, C., Ziegler, R. and Gross, M., "HSNets: Estimating Human Body Shape from Silhouettes with Convolutional Neural Networks," In International Conference on 3D Vision (3DV), 2016, 10 pages.

Dibra, E., Jain, H., Öztireli, C., Ziegler, R. and Gross, M., "Human Shape from Silhouettes Using Generative HKS Descriptors and Cross-Modal Neural Networks," In IEEE Conference on Computer Vision and Pattern Recognition (CVPR), 2017, 11 pages.

Dibra, E., Jain, H., Öztireli, C., Ziegler, R. and Gross, M., "Shape from Selfies: Human Body Shape Estimation Using CCA Regression Forests," In European Converence on Computer Vision (ECCV), 2016, 17 pages.

Gilbert, A., Volino, M., Collomosse, J. and Hilton, A.,"Volumetric Performance Capture from Minimal Camera View-Points," In European Conference on Computer Vision, 2018, 16 pages.

Gong, K., Liang, X., Zhang, D., Shen, X. and Lin, L., "Look into Person: Self-Supervised Structure-Sensitive Learning and a New Benchmark for Human Parsing," In IEEE Conference on Computer Vision and Pattern Recognition (CVPR), 2017, 9 pages.

Guan, P., Weiss, A., Bălan, A. O. and Black, M. J., "Estimating Human Shape and Pose from a Single Image," In IEEE International Conference on Computer Vision (ICCV), 2009, 8 pages.

Güler, R. A., Neverova, N. and Kokkinos, I., "DensePose: Dense Human Pose Estimation in the Wild," In IEEE Conference on Computer Vision and Pattern Recognition (CVPR), 2018, 10 pages.

He, K., Zhang, X., Ren, S. and Sun, J., "Deep Residual Learning for Image Recognition," In IEEE Conference on Computer Vision and Pattern Recognition (CVPR), 2016, 9 pages.

Horprasert, T., Harwood, D. and Davis, L. S., "A Statistical Approach for Real-Time Robust Background Subtraction and Shadow Detection," In IEEE International Conference on Computer Vision (ICCV), 1999, 19 pages.

Joo, H., Simon, T. and Y. Sheikh, Y., "Total Capture: A 3D Deformation Model for Tracking Faces, Hands, and Bodies," In IEEE Conference on Computer Vision and Pattern Recognition (CVPR), 2018, 10 pages.

Kanazawa, A., Black, M. J., Jacobs, D. W. and Malik, J., "End-to-End Recovery of Human Shape and Pose," In IEEE Conference on Computer Vision and Pattern Recognition (CVPR), 2018, 10 pages.

Krasin, I., Duerig, T., Alldrin, N., Ferrari, V., Abu-El-Haija, S., Kuznetsova, A., Rom, H., Uijlings, J., Popov, S., Kamali, S., Malloci, M., Pont-Tuset, J., Veit, A., Belongie, S., Gomes, V., Gupta, A., Sun, C., Chechik, G., Cai, D., Feng, Z., Narayanan, D., and Murphy, K., "Openimages: A Public Dataset for Large-Scale Multi-Label and Multi-Class Image Classification," Dataset available from https://storage.googleapis.com/openimages/web/index.html, 2017.

Kundu, A., Li, Y. and Rehg, J. M., "3D-RCNN: Instance-Level 3D Object Reconstruction via Render-and-Compare," in IEEE Conference on Computer Vision and Pattern Recognition (CVPR), 2018, 10 pages.

Lassner, C., Romero, J., Kiefel, M., Bogo, F., Black, M. J. and Gehler, P. V., "Unite the People—Closing the Loop Between 3D and 2D Human Representations," In IEEE Conference on Computer Vision and Pattern Recognition (CVPR), 2017, 10 pages.

Long, J., Shelhamer, E., and Darrell, T., "Fully Convolutional Networks for Semantic Segmentation, "In IEEE Conference on Computer Vision and Pattern Recognition (CVPR), 2015, 10 pages.

Loper, M., Mahmood, N., Romero, J., Pons-Moll, G. and Black, M. J., "SMPL: A Skinned Multi-Person Linear Model," ACM Trans. Graphics (Proc. SIGGRAPH Asia), 34(6):248:1-248:16, Oct. 2015, 16 pages.

Ngiam, J., Khosla, A., Kim, M., Nam, J., Lee, H.and Ng, A. Y., "Multimodal Deep Learning," In International Conference on Machine Learning (ICML), pp. 689-696, 2011, 8 pages.

Omran, M., Lassner, C., Pons-Moll, G., Gehler, P. V. and Schiele, B., "Neural Body Fitting: Unifying Deep Learning and Model-Based Human Pose and Shape Estimation," In International Conference on 3D Vision (3DV), 2018, 13 pages.

Pavlakos, G., Zhu, L., Zhou, X. and Daniilidis, K., "Learning to Estimate 3D Human Pose and Shape from a Single Color Image," In IEEE Conference on Computer Vision and Pattern Recognition (CVPR), 2018, 10 pages.

Popa, A.-I., Zanfir, M. and C. Sminchisescu, C., "Deep Multitask Architecture for Integrated 2D and 3D Human Sensing," In IEEE Conference on Computer Vision and Pattern Recognition (CVPR), 2017, 10 pages.

Rhodin, H., Robertini, N., Casas, D., Richardt, C., Seidel, H.-P. and Theobalt, C., "General Automatic Human Shape and Motion Capture Using Volumetric Contour Cues," In European Conference on Computer Vision, 2016, 18 pages.

Robinette, K. M., Blackwell, S., Daanen, H., Boehmer, M., Fleming, S., Brill, T., Hoeferlin, D. and Burnsides, D., "Civilian American and European Surface Anthropometry Resource (CAESAR) Final Report," Tech. Rep. AFRL-HEWP-TR-2002-0169, US Air Force Research Laboratory, 2002, 70 pages.

Sigal, L., Bălan, A. O. and Black, M. J., "Combined Discriminative and Generative Articulated Pose and Non-Rigid Shape Estimation," In Neural Information Processing Systems (NIPS), 2007, 8 pages.

Sun, J., Ovsjanikov, M. and Guibas, L., "A Concise and Provably Informative Multi-Scale Signature Based on Heat Diffusion," In Symposium on Geometry Processing, 2009, 10 pages.

Tan, J. K. V., Budvytis, I. and Cipolla, R., "Indirect Deep Structured Learning for 3D Human Body Shape and Pose Prediction," In British Machine Vision Conference, 2017, 11 pages.

TC2 Labs LLC, "SizeUSA", 3 pages, http://scan2fit.com/sizeusa/about.php.

Varol, G., Ceylan, D., Russell, B., Yang, J., Yumer, E., Laptev, I. and Schmid, C., "BodyNet: Volumetric Inference of 3D Human Body Shapes," In European Conference on Computer Vision (ECCV), 2018, 17 pages.

(56) References Cited

OTHER PUBLICATIONS

Varol, G., Romero, J., Martin, X., Mahmood, N., Black, M. J., Laptev, I. and Schmid, C., "Learning from Synthetic Humans," In IEEE Conference on Computer Vision and Pattern Recognition (CVPR), 2017, 9 pages.

Xi, P., Lee, W.-S. and Shu, C., "A Data-Driven Approach to Human-Body Cloning Using a Segmented Body Database," In Pacific Conference on Computer Graphics and Applications (PG), 2007, 9 pages.

Yu, F., Zhang, Y., Song, S., Seff, A., and Xiao, J., "LSUN: Construction of a Large-Scale Image Dataset Using Deep Learning with Humans in the Loop," arXiv preprint arXiv:1506.03365, 2015, 9 pages.

Zanfir, A., Marinoiu, E. and Sminchisescu, C., "Monocular 3D Pose and Shape Estimation of Multiple People in Natural Scenes—the Importance of Multiple Scene Constraints," In IEEE Conference on Computer Vision and Pattern Recognition (CVPR), 2018, 10 pages.

Zhang, H., Dana, K., Shi, J., Zhang, Z., Wang, X., Tyagi, A. and Agrawal, A., "Context Encoding for Semantic Segmentation," In the IEEE Conference on Computer Vision and Pattern Recognition (CVPR), Jun. 2018, 10 pages.

\* cited by examiner

WEARABLE DEVICE BATTERY CONSERVATION

BACKGROUND

Wearable devices are increasing in popularity. Many of the current devices include sensors that are operable to measure a variety of metrics about the user wearing the device. Metrics include heartrate, blood pressure, motion, step count, sleep quality, etc. Many current systems simply report the collected metrics to the user, for example, over a period of time. Each of these devices utilize a battery to power the components within the devices that collected the various items of information.

BRIEF DESCRIPTION OF DRAWINGS

The detailed description is described with reference to the accompanying figures.

DETAILED DESCRIPTION

Figure 1:
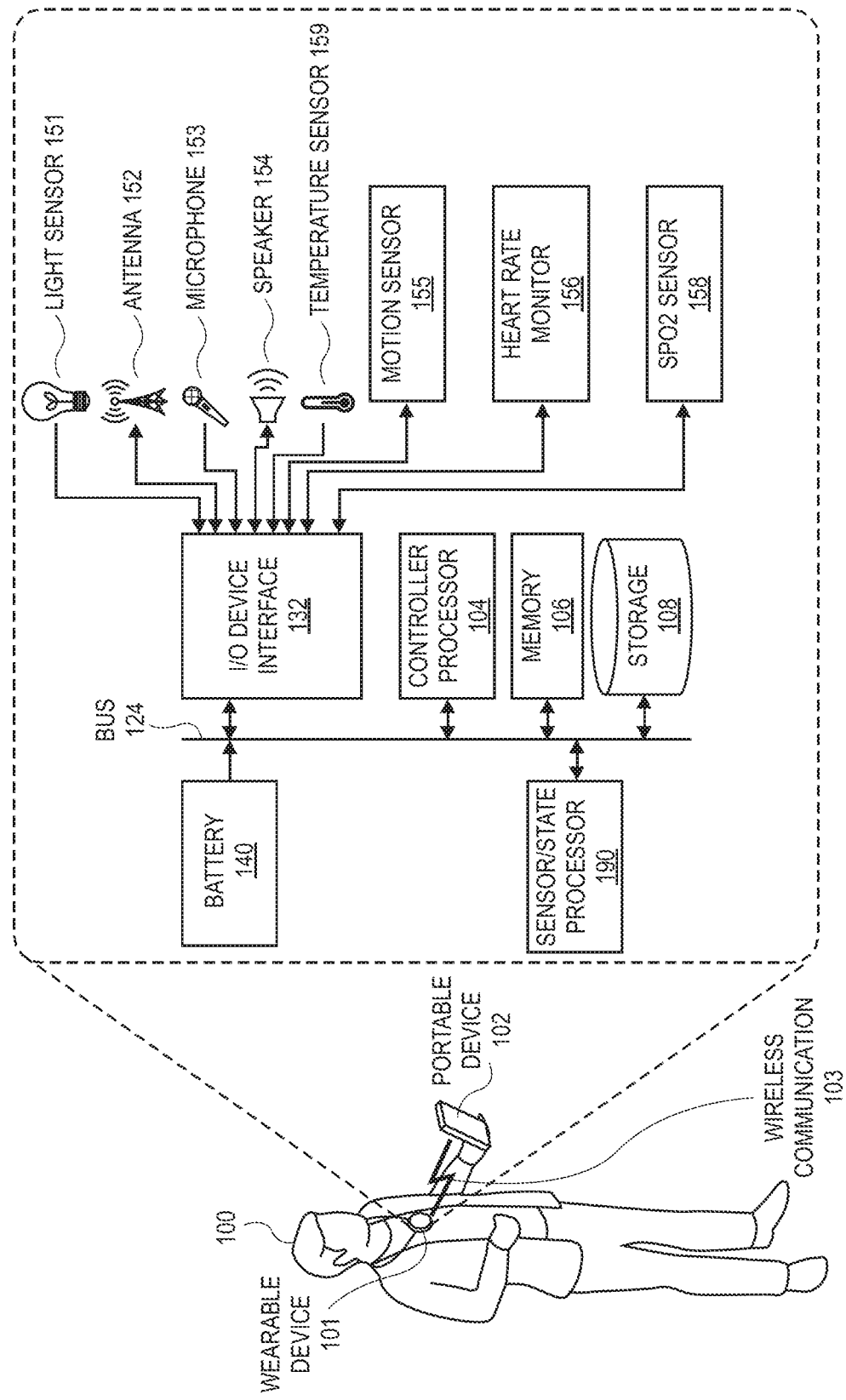
FIG. 1 is an example diagram of a wearable device apparatus and a portable device of a user, in accordance with described implementations.

Described is a wearable device apparatus that is operable to reduce battery consumption based on a determined state of a user wearing the wearable device. For example, based on the determined state of the user, one or more components may be transitioned from an active state to a low power state, or from the low power state to the active state. As another example, the processing frequency of some or all of the sensor data collected by sensors of the wearable device may be increased or decreased based on the determined state of the user and/or the wireless transmission of data from the wearable device may be increased or decreased based on the state of the user. For example, if the user is in a sleep state, rather than continuing to wirelessly send data from the wearable device to a portable device associated with the user, a buffer size of a buffer in a memory of the wearable device may be increased, the wireless connection between the wearable device and a portable device terminated, and collected sensor data stored in the increased capacity buffer while the user is in the sleep state. At some point prior to a completion of the sleep state, which may be determined, for example, based on a predicted sleep state duration and/or based on sensor data that indicates that the user is exiting the sleep state, the wearable device may re-establish the wireless connection with the portable device and send the collected and stored sensor data to the portable device. Likewise, in some implementations, during the sleep state, the processor of the wearable device may be transitioned to the low power state. Similarly, at a point prior to the user exiting the sleep state, the processor may be transitioned back to the active state and process the collected and stored sensor data to produce processed sensor data that is sent to the wearable device.

In still other examples, the sampling rate of some or all of the sensors and/or the processing frequency of some or all of the sensor data by the processor may also be adjusted based on the determined state of the user. For example, the sampling frequency and/or processing frequency of sensor data that is not likely to change more than an immaterial amount, or be of much interest to the user during a particular state, may be decreased to conserve battery. As one illustrative example, when the user is determined to be in a sedentary state, the frequency of collection and/or processing of sensor data such as heartrate, blood pressure, step count, etc., which are unlikely to change much during a sedentary state, may be reduced. In comparison, when the user is in an active state, the frequency of sensor data collection and/or processing of sensor data may be increased to provide finer grained information to the user during those active states. However, in some instances, if it is determined that the user is unlikely to access an application executing on the portable device during the active state to view the data, the processing and/or wireless transmission of that data may be delayed or bundled to reduce the frequency of processing and/or transmission of the data during the active state, thereby conserving battery power of the wearable device. Many other examples of conserving battery power of a wearable device based on a determined state of the user are discussed further below.

It is worth noting that in the disclosed implementations, the collected data by sensors of the wearable device apparatus described herein may not be sent to any remote computing systems and all processing of the sensor data discussed herein may be performed on the wearable device apparatus alone, on the portable device alone, or on a combination of the wearable device apparatus and the portable device. For example, in some implementations, the wearable device may process the sensor data and include a display and/or audio output that is used to present information relating to the processed sensor data to the user. In other implementations, with approval from the user, some or all of the sensor data and/or processed data may be sent to one or more remote computing resources.

As discussed further below, the disclosed implementations provide a technical improvement to battery/power conservation and operability of a wearable device apparatus worn by a user. In some implementations, a wearable device, such as the wearable device apparatus discussed below with respect to FIG. 1, utilizing the disclosed implementations, may operate on a single battery charge for ten or more days while at the same time collecting sensor data corresponding to a user that is wearing the wearable device and/or the environment surrounding the user. In comparison, without use of the disclosed implementations, the same device operating to collect similar types of sensor data would only be able to operate on a single battery charge for three to five days.

FIG. 1 is an example diagram of a wearable device apparatus 101 and a portable device 102 of a user 100, in accordance with described implementations.

The portable device 102 may be any type of portable device, including, but not limited to, a cellular phone (aka smart phone), tablet, touch-pad, laptop, etc. As discussed further below with respect to FIGS. 11-12, the portable device may include a display, such as a touch-based display and a wireless communication interface, such as 802.15.4 (ZIGBEE), 802.11 ("WI-FI"), 802.16 ("WiMAX"), BLUETOOTH, Z-WAVE, Near Field Communication ("NFC"), etc., to enable wireless communication 103 with the wearable device 101.

The wearable device apparatus 101 may be any form of wearable device. For example, the wearable device apparatus may be in the form of a wristband, a necklace (as illustrated in FIG. 1), headphones, a ring, a watch, an earring, a headband, glasses, an article of clothing, an on-skin apparatus (e.g., an adhesive patch), etc.

In operation, the wearable device 101 may include a battery 140 and/or other power source, computer-readable and computer-executable instructions, one or more sensor/state processors 190 that may include a central processing unit (CPU) 104 for processing sensor data, computer-readable instructions, etc., and a memory 106 for storing data and instructions of the wearable device apparatus. The memory 106 may individually include volatile random access memory (RAM), non-volatile read only memory (ROM), non-volatile magnetoresistive (MRAM) and/or other types of memory. The wearable device 101 may also include a data storage component 108 for storing data, controller/processor-executable instructions, monitoring schedules, user state related information (e.g., predicted state durations), etc. Each data storage component may individually include one or more non-volatile storage types such as magnetic storage, optical storage, solid-state storage, etc.

Computer instructions for operating the wearable device 101 and its various components may be executed by the controller(s)/processor(s) 104, using the memory 106 as temporary "working" storage at runtime. A wearable device's 101 computer instructions may be stored in a non-transitory manner in non-volatile memory 106, storage 108, or an external device(s). Alternatively, some or all of the executable instructions may be embedded in hardware or firmware on the wearable device 101 in addition to or instead of software.

The wearable device 101 also includes an input/output device interface 132. A variety of components may be connected through the input/output device interface 132. Additionally, the wearable device 101 may include an address/data bus 124 for conveying data among components of the wearable device. Each component within the wearable device 101 may also be directly connected to other components in addition to (or instead of) being connected to other components across the bus 124.

The wearable device 101 may be "headless" and may primarily rely on spoken commands for input and/or through interaction with one or more control interfaces or buttons. In other examples, the wearable device 101 may include a display, which may allow a touch-based interface. The wearable device 101 may also include input/output device interfaces 132 that connect to a variety of components such as an audio output component, such as a speaker 154. The wearable device 101 may also include an audio capture component. The audio capture component may be, for example, a microphone 153 or array of microphones, etc.

The microphone 153 may be configured to capture audio, such as environmental noises, voices, etc. As noted above, in some implementations, the wearable device 101 may also include a display and/or an audio output (e.g., speaker).

The wearable device 101 may also include other sensors that collect sensor data that may be representative of user data and/or the environment in which the user is located. Any number and/type of sensors may be included in the device. In the illustrated example, in addition to the microphone, the wearable device 101 may include a light sensor 151 that may measure the ambient light, one or more temperature sensors 159 that may measure the ambient temperature and/or measure the temperature of the user when wearing the wearable device, a motion sensor 155, such as an accelerometer, gyroscope, etc., to measure movement of the user, a heartrate monitor 156 to measure the heartrate of the user, an SpO2 sensor 158 to measure the saturation percentage of oxygen in the blood, a blood pressure sensor, and/or other sensors/monitors to measure other user data and/or environment data.

The wireless device 101 may also include a communication interface, such as an antenna 152 to enable wireless communication 103 between the wearable device 101 and the portable device 102. Any form of wireless communication may be utilized to facilitate communication between the wearable device 101 and the portable device 102, and/or other device local to the user and/or associated with the user. For example, any one or more of ZIGBEE, WI-FI, WiMAX, BLUETOOTH, Z-WAVE, NFC, etc., may be used to communicate between the wireless device 101 and the portable device 102, etc. For example, the wearable device 101 may be configured to transmit sensor data and/or processed data received from the wearable device 101.

Each of the components of the wearable device 101 may be powered by the power supply of the wearable device, such as the battery 140. With the disclosed implementations, one or more of the components of the wearable device 101 may transition between a low power state, during which the component consumes little if any power from the power source (e.g., battery), and an active state where the component is operational. Transitioning components of the wearable device 101 between the low power state and the active state conserves power and extends the operability of the wearable device 101 before the power supply of the wearable device must be recharged. Likewise, as discussed further below, some or all of the sensors may be adjustable such that the collection frequency of data may be increased or decreased. Alternatively, or in addition thereto, the frequency of processing of the sensor data to produce processed data and/or the wireless transmission of sensor data/processed data may be altered, for example, based on the determined state of the user wearing the wearable device. The antenna and transmitter that is used to wirelessly transmit data to/from the wearable device 101 is generally referred to herein as a wireless transmitter.

While the above example references both sensors and monitors that collect data about a user and/or the environment, for ease of discussion, unless explicitly stated otherwise, sensors, as used herein, generally refers to sensors and/or monitors that collect data, referred to herein generally as sensor data, corresponding to a user or the environment.

Figure 2:
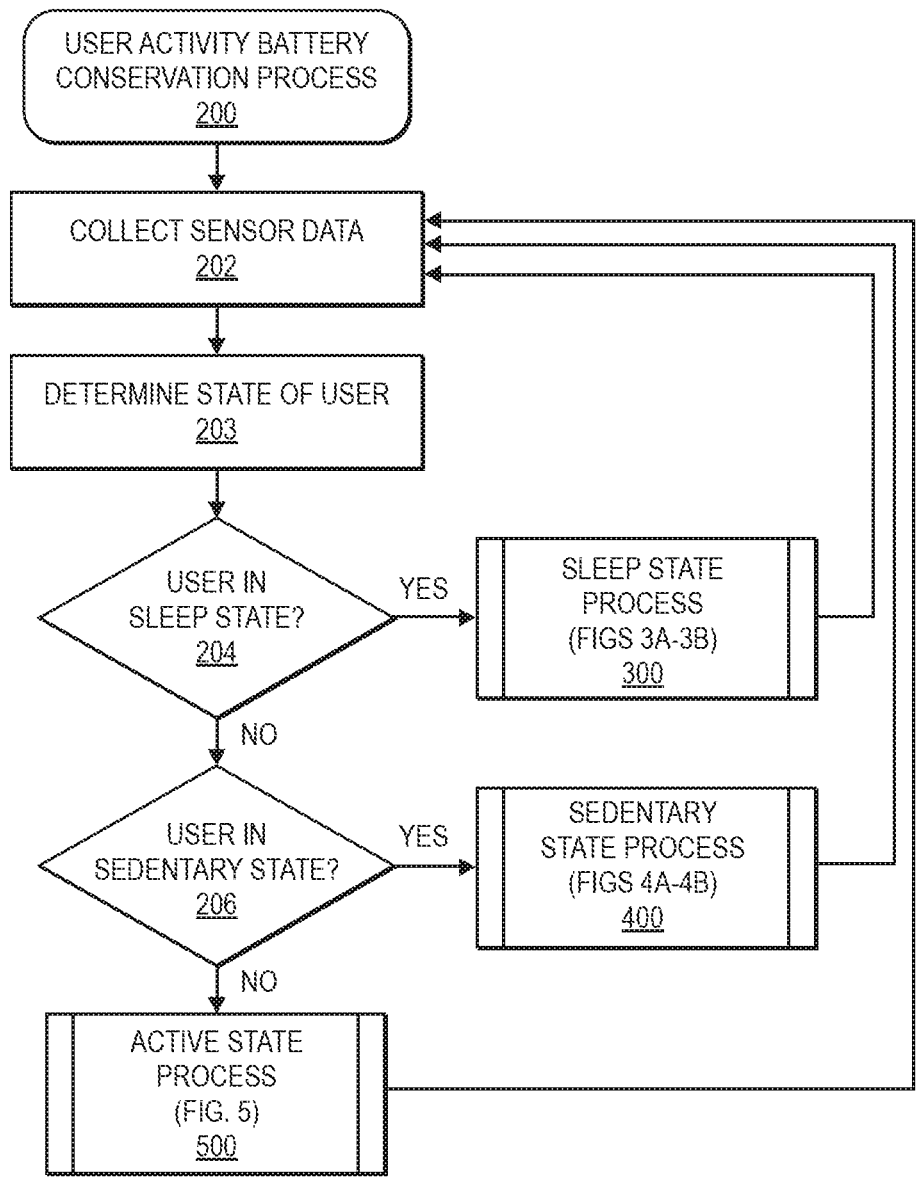
FIG. 2 is an example user activity battery conservation process, in accordance with described implementations.

FIG. 2 is an example user activity battery conservation process 200, in accordance with described implementations.

The example process begins with the collection of sensor data by the one or more sensors of the wearable device apparatus, as in 202. As discussed above, the wearable device may include any of a variety of sensors that include, but are not limited to, sensors that monitor data (e.g., motion, steps, heartbeat, SpO2, temperature, mood, etc.) corresponding to the user wearing the wearable device as well as environment data (e.g., temperature, humidity, light, etc.) about the environment in which the user is located.

Based at least in part on the sensor data collected that relates to the user, such as movement, heartrate, perspiration, blood pressure, breathing pattern, etc., the state of the user is determined, as in 203. In the examples discussed herein, the user may be in any of three states—sleep state, sedentary state, or active state. However, it will be appreciated that in other implementations, there may be fewer or additional states for the user. During an active state, the user is active (e.g., exercising) and may have an elevated heartrate, elevated breathing, increased movement/steps, etc. In a sedentary state, in comparison, the user may have a resting heartrate that does not change much, a resting blood pressure, a normal breathing pattern, low movement or step count, etc. Finally, in a sleep state, the user may have still a lower resting heartrate, the user's heartrate pattern may change, the user may exhibit slower breathing, less movement, etc.

Figure 3A:
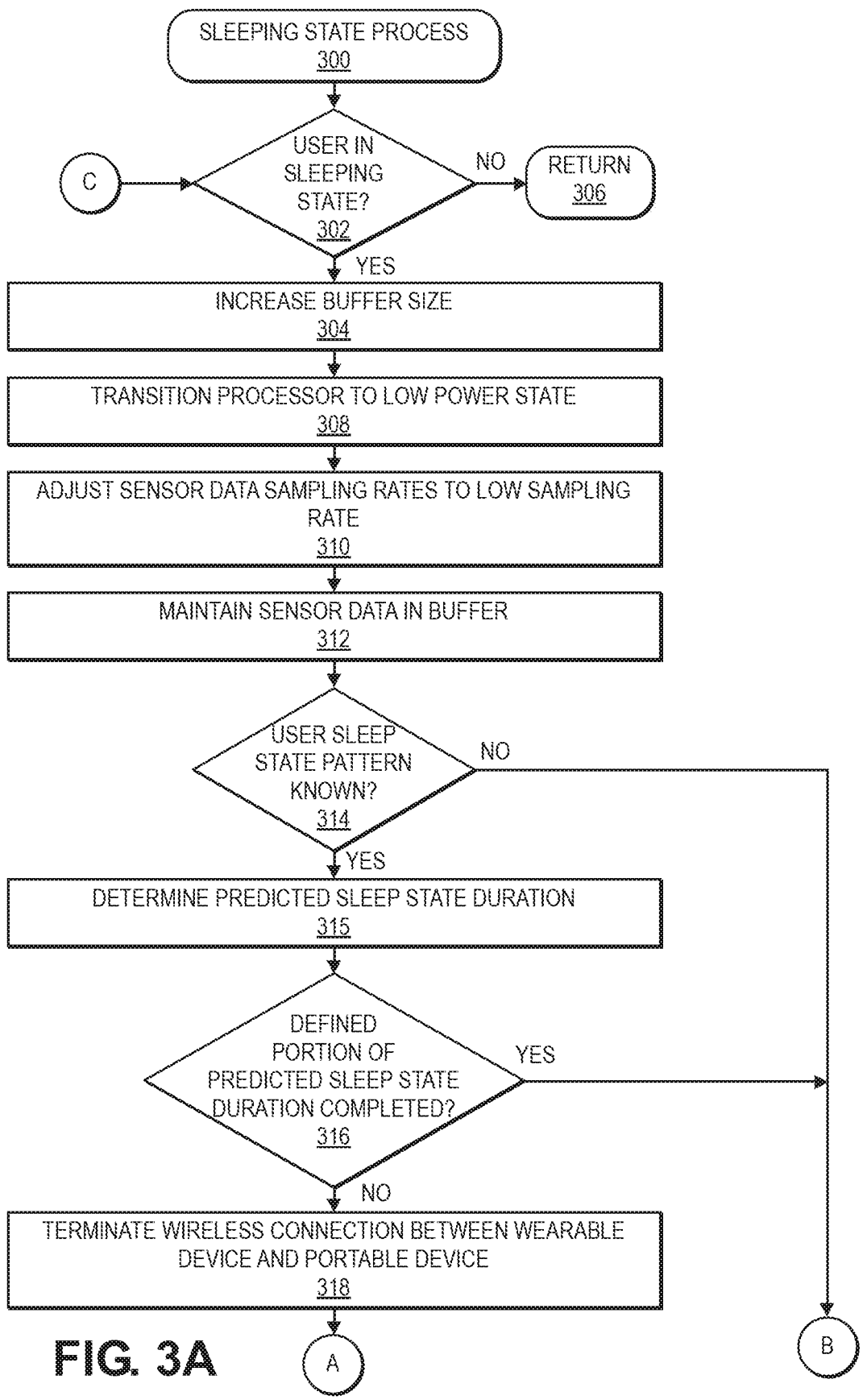
FIGS. 3A through 3B is an example sleep state process, in accordance with described implementations.
Figure 3B:
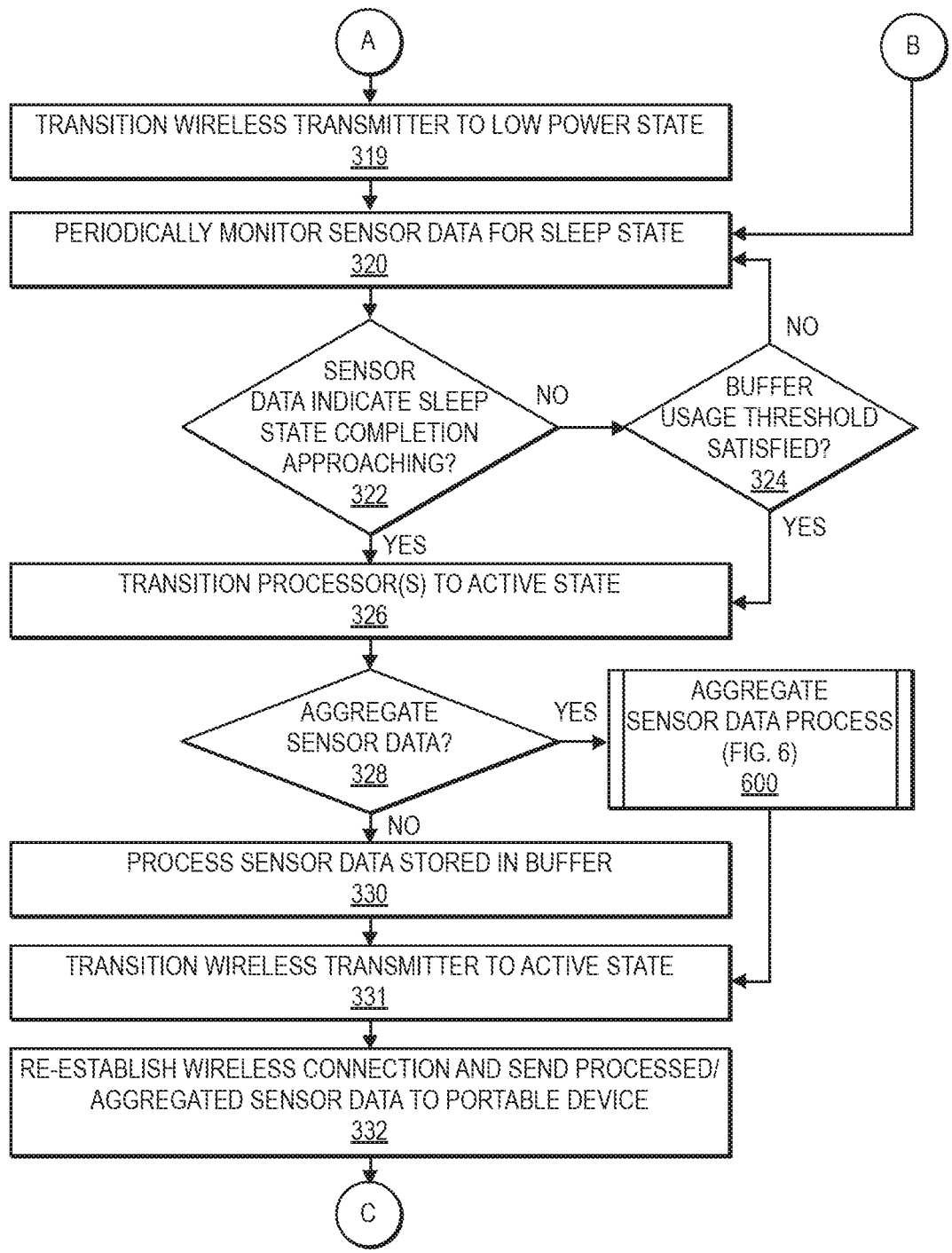
Figure 4A:
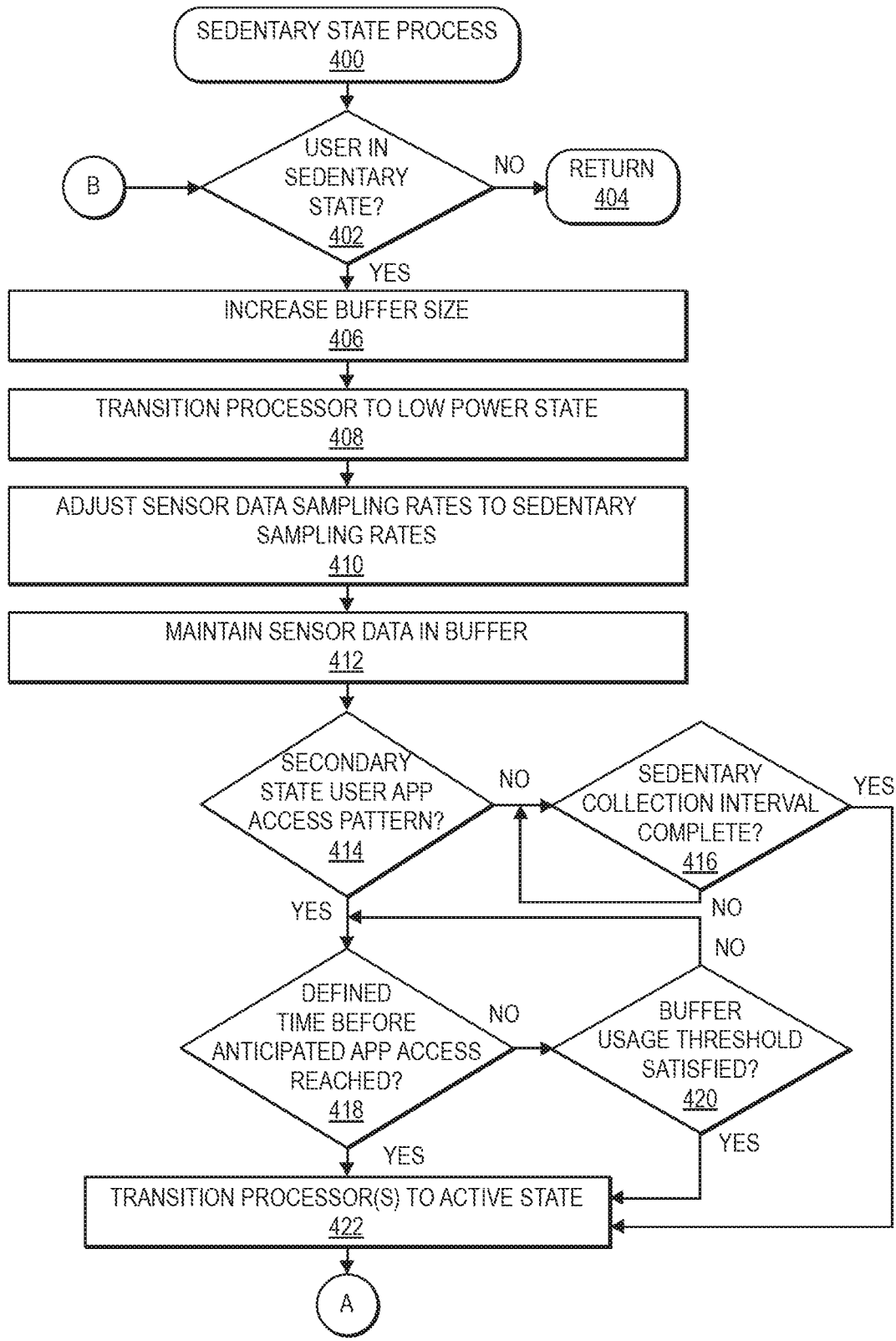
FIGS. 4A through 4B is an example user sedentary state process, in accordance with described implementations.
Figure 4B:
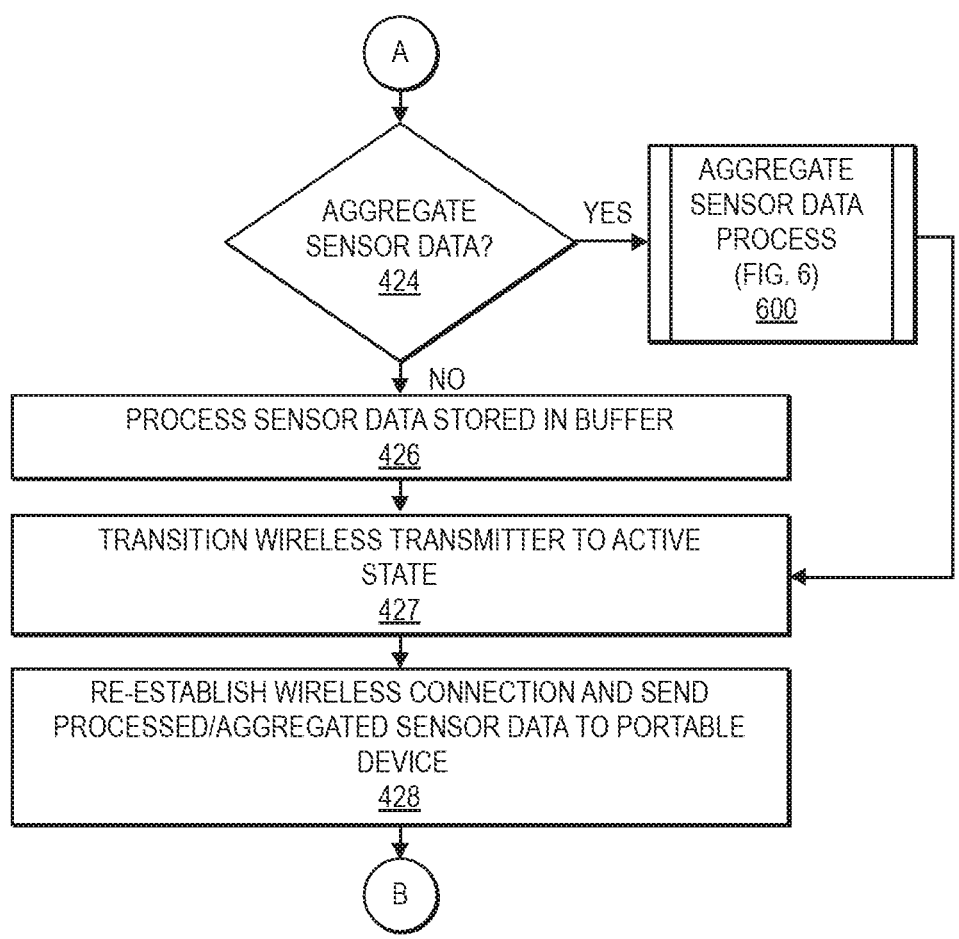
Figure 5:
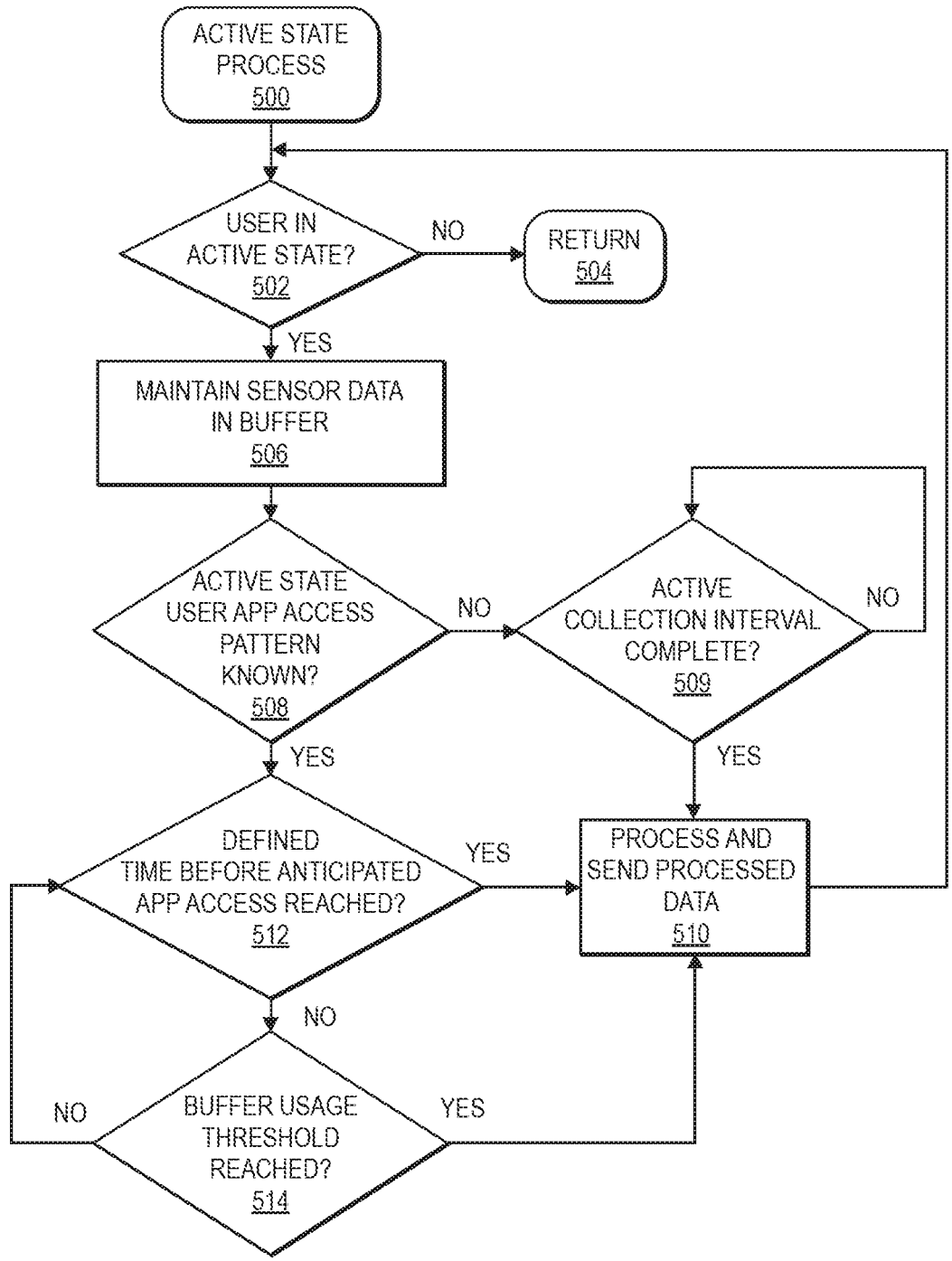
FIG. 5 is an example user active state process, in accordance with described implementations.

A determination is then made as to whether the user is in a sleep state, as in 204. If it is determined that the user is in a sleep state, the sleep state process 300, discussed below with respect to FIGS. 3A through 3B, is performed. If the user is not in a sleep state, it is determined whether the user is in a sedentary state, as in 206. If the user is in a sedentary state, the sedentary state process 400, discussed below with respect to FIGS. 4A through 4B, is performed. Finally, if it is determined that the user is not in the sleep state and not in the sedentary state, in this example meaning that the user is in the active state, the active state process 500, discussed below with respect to FIG. 5, is performed.

Upon completion and return of the sleep state process 300, the sedentary state process 400, or the active state process 500, the example process 200 returns to block 202 and continues. The example process 200, and each of the related processes discussed herein may be continually performed by the example wearable device to conserve battery power of the wearable device while worn by the user.

FIG. 3A through 3B is an example sleep state process 300, in accordance with described implementations.

The example process 300 begins in response to a determination that a user is in a sleep state and may itself continually or periodically confirm, based at least in part on the sensor data, that the user is in the sleep state, as in 302. If it is determined that the user is not in the sleep state, the example process 300 returns to the example process 200 with an indication that the user is not in a sleep state, as in 306.

However, if it is determined that the user is in a sleep state, a buffer size of a buffer in a memory of the wearable device is increased from a first size that may be used during an active state and/or the sedentary state so that more sensor data can be stored in the buffer during the sleep state, as in 304. For example, if the buffer is 5 megabytes when the user is in an active state, the buffer size may be increased to 14 megabytes while the user is in the sleep state so that additional sensor data may be stored in the buffer. In other implementations, the buffer size may be larger or smaller in any of the different states.

Still further, the one or more processors of the wearable device may be transitioned to a low power state to conserve battery power of the wearable device while the user is in a sleep state, as in 308. By increasing the buffer size of the buffer while the user is in the sleep state, additional raw sensor data can be stored, thereby prolonging the interval between any processing that needs to be performed by the one or more processors. Therefore, the one or more processors may be maintained in the low power state for longer periods of time. Alternatively, or in addition thereto, the enlarged buffer may be used to store processed data, thereby prolonging the interval between any transmission of data by the wireless transmitter. For example, in some implementations, the one or more processors may periodically transition out of the low power state, process collected sensor data and transition back to the low power state. Rather than transmitting the processed data each time it is generated by the processor, the processed data may be stored in the buffer and multiple sets of processed data wirelessly transmitted during a single wireless connection, as discussed below.

In addition, the sensor data sampling rate of some or all of the sensors of the wearable device may be reduced from a normal sampling rate to a low sampling rate, as in 310. In one implementation, only sensors that collect data relating to user information that will not likely change beyond a defined range (e.g., ±2.5%) may be set to a lower sampling rate. In other implementations, all sensors may be set to a low sampling rate. For example, if sensors typically sample at a rate of 25 hertz ("Hz"), referred to herein as a normal sampling rate, the low sampling rate may be 15 Hz. In other implementations, the normal sampling rate and/or the low sampling rate may be different than 25 Hz and 15 Hz, higher or lower. By transitioning some or all of the sensors to a low sampling rate during a sleep state of the user, less power is consumed by the sensors and sensor data can be collected from the sensors for a longer period of time before the buffer exceeds a defined buffer usage threshold (discussed below) and/or before data needs to be processed/wirelessly transmitted to the portable device. In comparison, lowering sampling for sensors that will not likely collect data that represents a measurable change during the sleep state, little information is lost with the lower sampling rates. In some implementations, the user may select which sensors may be transitioned into a low sampling rate during sleep states of the user.

In some implementations, rather than or in addition to lowering the sampling rate for one or more sensors, as discussed further below, processing of the data may be altered to only process some of the data and/or the data may be aggregated.

As the data from the sensors is collected, the sensor data may be stored, without further processing, in the buffer of the memory of the wearable device, as in 312.

In addition, a determination may be made as to whether a user sleep state pattern is known, as in 314. A user sleep state pattern may be determined based on prior sleep states experienced by the user, based on a location of the user during those prior sleep patterns, based on a time of day of the prior sleep patterns, etc. For example, if the user regularly experiences a sleep state between 20:00 hours and 06:00 hours, seven days a weeks when the user is located at a similar location (e.g., home), a user sleep state pattern may be established for that period of time at that location. If the user transitions into a sleep state at that location and around that time window, the user sleep pattern may be determined to be known. In comparison, if the user transitions into a sleep state while riding a bus and the user does not typically enter a sleep state while riding the bus, even though the sleep state pattern of the user between 20:00 hours and 06:00 hours when the user is at home may be known, it may be determined that no sleep pattern is known for the user when the user is on the bus and transitions to the sleep state. As still another example, the user sleep state pattern may be determined based on supplemental information provided by the user and/or obtained from user associated applications (e.g., calendar, email) for which the user has allowed access. In some implementations, historical user sleep patterns, supplemental information, etc., about the user may be provided to a machine learning model to determine sleep state patterns for the user. As noted above, the sleep state patterns may be based on a variety of factors including, but not limited to, time of day, day of week, location, food intake, alcohol consumption, supplemental information about the user (e.g., calendar entries), etc.

Returning to FIG. 3A, if it is determined that the user sleep state pattern is known, a predicted sleep state duration for the current sleep state of the user is determined, as in 315. The predicted sleep state duration may be determined based on information known about the user and prior sleep states of the user. For example, sensor data collected about the user prior to the transition of the user into the sleep state, along with the sleep state pattern, may be used, for example, by a machine learning system to determine a predicted sleep state duration.

Based on the determined sleep state duration, a determination is made as to whether a defined portion of a predicted sleep state duration has completed, as in 316. The defined portion may be a percentage (e.g., 98%) of the total predicted sleep state duration and/or a defined period of time before the predicted completion of the sleep state duration (e.g., five minutes). As discussed below, the purpose of determining whether a defined portion of the predicted sleep state duration has completed is to allow for the data stored in the buffer during the sleep state to be processed and/or transmitted from the wearable device to the portable device before the user exits the sleep state and accesses an application executing on the portable device to view information relating to the collected sensor data.

If it is determined that the defined portion of the predicted sleep state duration has not completed, the wireless connection between the wearable device and the portable device is terminated to conserve battery power of the wearable device, as in 318. For example, if the wireless connection between the wearable device and the portable device is BLUETOOTH, which typically includes periodic transmission of signals between devices to maintain the connection, the connection may be completely terminated. Other wireless protocols may likewise be terminated such that no wireless connection between the wearable device and the portable device remains. In addition to terminating the wireless connection, the wireless transmitter of the wearable device may also be transitioned to a low power state to reduce power consumed by the wireless transmitter, as in 319.

After terminating the wireless connection and transitioning the wireless transmitter to a low power state, or if it is determined that the user sleep pattern is not known, or if it is determined that the defined portion of the predicted sleep state duration has completed, the sensor data collected while the user is in the sleep state is periodically monitored for sleep state indicators, as in 320. As discussed above, when the user is in a sleep state, some sensor data may not change beyond a measurable amount. If the sensor data remains constant, it may be confirmed that the user is still in the sleep state. However, if the sensor data begins to change, for example the user's heartrate begins to increase, the user's heartrate pattern changes, the user's breathing pattern changes, the user begins to move more, etc., it may be determined that a completion of the sleep state, also referred to herein as a sleep state completion, is approaching.

Based on the sensor data, a determination is made as to whether the sensor data indicates that the sleep state completion of the sleep state of the user is approaching, as in 322. If it is determined that the sleep state completion is not approaching, a determination is made as to whether the buffer usage threshold has been satisfied, as in 324. The buffer usage threshold may be a percentage of the buffer size, an amount of the buffer size, etc., and may vary based on, for example, an expected wireless connection probability, discussed further below, based on user preference, based on time until a predicted sleep state completion, etc.

Figure 6:
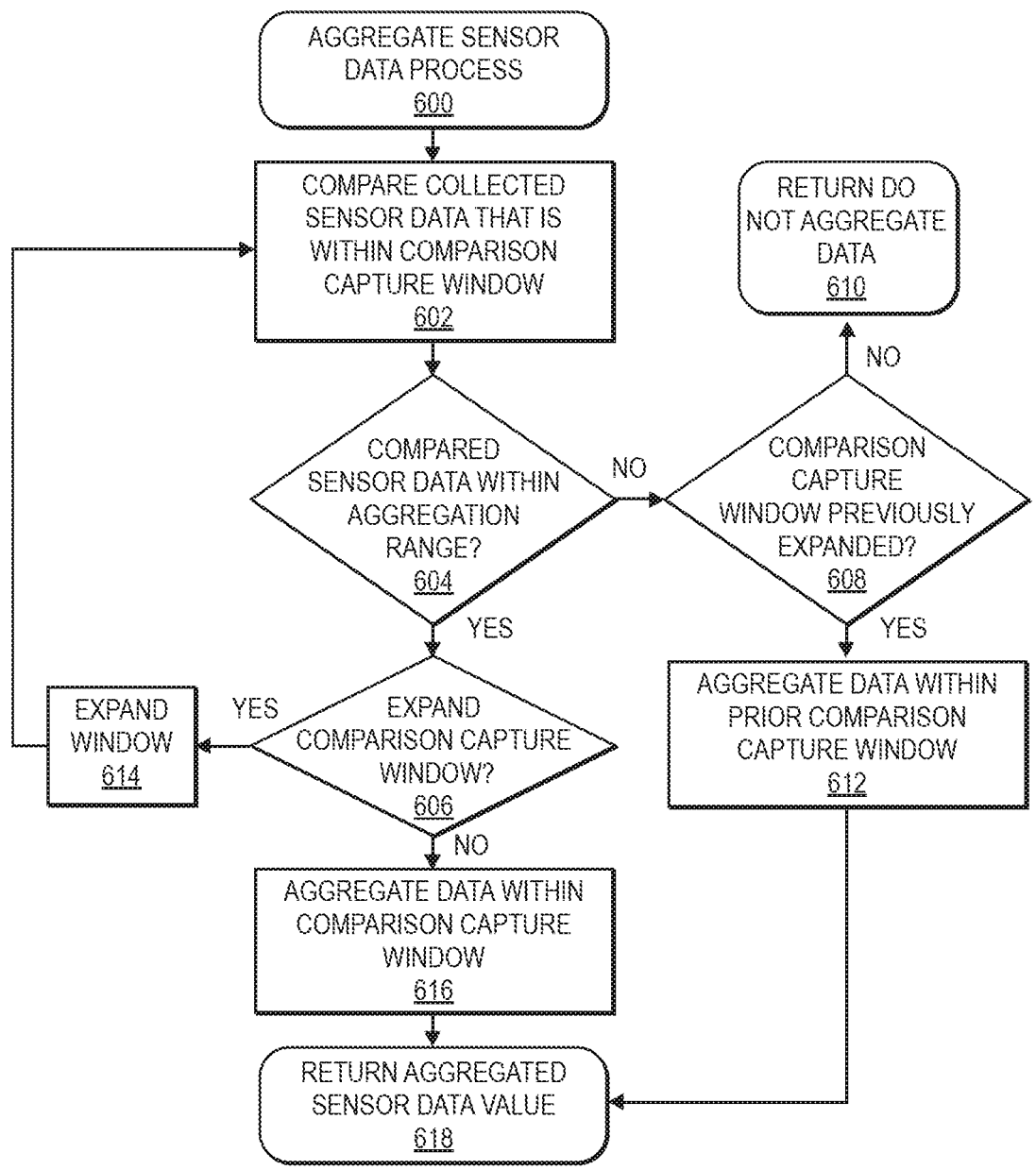
FIG. 6 is an aggregate sensor data process, in accordance with described implementations.

If it is determined that the buffer usage threshold has not been satisfied, the example process 300 returns to block 320 and continues. In comparison, if it is determined that the buffer usage threshold has been satisfied or that the sensor data indicates that the sleep state completion is approaching, the processor(s) of the wearable device may be transitioned to an active state, as in 326. A determination may also be made as to whether some or all of the sensor data is to be aggregated, as in 328. If it is determined that some or all of the sensor data is to be aggregated, for the sensor data that is to be aggregated, the example aggregate sensor data process 600, discussed below with respect to FIG. 6, is performed, as in 600. If it is determined that the sensor data is not to be aggregated, or that a portion of the sensor data is not to be aggregated, the sensor data that was collected during the sleep state and stored in the buffer that is not to be aggregated may be processed by the processor to produce processed data, as in 330.

In addition, the wireless transmitter is also transitioned back to the active state, as in 331, and the wireless connection between the wearable device and the portable device is re-established (or a new wireless connection is established), as in 332. Upon establishment of the wireless connection between the wearable device and the portable device associated with the user, the processed sensor data and/or the aggregated sensor data, returned from example process 600, is sent from the wearable device, via the wireless connection, to the portable device, as in 332. As discussed above, in some implementations, the processor may periodically transition to the active state and process the collected sensor data without transitioning the wireless transmitter to the active state and wirelessly transmitting the processed data. For example, in some implementations, the processor may continue to cycle between a low power state and an active state to process sensor data and the processed data stored in the buffer. At a different interval, it may be determined that the wireless transmitter is to be activated and the processed data wirelessly transmitted from the wearable device.

Finally, the example process 300 returns to block 302 and continues.

FIGS. 4A through 4B is an example user sedentary state process 400, in accordance with described implementations.

The example process 400 begins in response to a determination that a user is in a sedentary state and may itself continually or periodically confirm, based at least in part on the sensor data, that the user is in the sedentary state, as in 402. If it is determined that the user is not in the sedentary state, the example process 400 returns to the example process 200 with an indication that the user is not in a sedentary state, as in 404.

However, if it is determined that the user is in a sedentary state, a buffer size of a buffer in a memory of the wearable device is increased from a first size that may be used during an active state so that more sensor data can be stored in the buffer during the sedentary state, as in 406. For example, if the buffer is 5 megabytes when the user is in an active state, the buffer size may be increased to 10 megabytes while the user is in the sedentary state so that additional sensor data may be stored in the buffer. In other implementations the buffer size may be larger or smaller in any of the different states. In some implementations, different buffer sizes may be associated with different sedentary states. For example, the active state may be associated with a first buffer size, the sedentary state may be associated with a second buffer size that is larger than the first buffer size, and the sleep state may be associated with a third buffer size that is larger than the second buffer size.

Still further, the one or more processors of the wearable device may be transitioned to a low power state to conserve battery power of the wearable device while the user is in a sedentary state, as in 408. By increasing the buffer size of the buffer while the user is in the sedentary state, additional raw sensor data can be stored, thereby prolonging the interval between any processing that needs to be performed by the one or more processors. Therefore, the one or more processors may be maintained in the low power state for longer periods of time. Alternatively, or in addition thereto, the enlarged buffer may be used to store processed data, thereby prolonging the interval between any transmission of data by the wireless transmitter. For example, in some implementations, the one or more processors may periodically transition out of the low power state, process collected sensor data and transition back to the low power state. Rather than transmitting the processed data each time it is generated by the processor, the processed data may be stored in the buffer and multiple sets of processed data wirelessly transmitted during a single wireless connection, as discussed below.

In addition, the sensor data sampling rate of some or all of the sensors of the wearable device may be reduced from a normal sampling rate to a low sampling rate, as in 410. In one implementation, only sensors that collect data relating to user information that will not likely change beyond a defined range (e.g., ±2.5%) during a sedentary state may be set to a lower sampling rate. For example, sensors that collect sensor data relating to a user step count, heartrate, blood pressure, etc., which are unlikely to change beyond a defined threshold, may be adjusted to a low power state.

In other implementations, all sensors may be set to a low sampling rate. For example, if sensors typically sample at a rate of 25 hertz ("Hz"), referred to herein as a normal sampling rate, the low sampling rate may be 15 Hz. In other implementations, the normal sampling rate and/or the low sampling rate may be different than 25 Hz and 15 Hz, higher or lower. By transitioning some or all of the sensors to a low sampling rate during a sedentary state of the user, less power is consumed by the sensors and sensor data can be collected from the sensors for a longer period of time before the buffer exceeds a defined usage threshold and/or before data needs to be processed/wirelessly transmitted to the portable device. In comparison, lowering sampling for sensors that will not likely collect data that represents a measurable change during the sedentary state, little information is lost with the lower sampling rates. In some implementations, the user may select which sensors may be transitioned into a low sampling rate during sedentary states of the user.

In some implementations, rather than or in addition to lowering the sampling rate for one or more sensors, as discussed further below, processing of the data may be altered to only process some of the data and/or the data may be aggregated. For example, the one or more processors may continue to periodically process the sensor data. However, during the sedentary state, the processed data may be compared to previously processed data that is stored in the buffer of the wearable device and, if the data has not changed, the processed data may be discarded, thereby keeping the buffer available for changes in processed data.

As the data from the sensors is collected, the sensor data may be stored, without further processing, in the buffer of the memory of the wearable device, as in 412.

A determination may also be made as to whether a sedentary state user application access pattern is known for the user, as in 414. A sedentary state user application access pattern may be a pattern at which the user generally or predictably accesses, during a sedentary state, an application executing on the mobile device to view information representative of sensor data collected by sensors of the wearable device during the sedentary state. In some implementations, the sedentary state user application access pattern may be determined by a machine learning model that uses prior user application access patterns, locations of the user during sedentary states and/or application access, duration of application accesses, duration of sedentary states, etc., to predict a sedentary state user application access pattern.

If it is determined that the sedentary state user application access pattern is not known for the user, a determination is made as to whether a sedentary collection interval is complete, as in 416. A sedentary collection interval may be a defined interval of time during the sedentary state in which sensor data is collected and stored in the buffer of the wearable device before processing and/or transmitting to the portable device. A processing/transmission point may occur upon completion of each defined sedentary collection interval so that the data stored in the buffer during the immediately prior collection interval can be processed and/or transmitted from the wearable device to the portable device to free up buffer usage and so that information representative of the collected sensor data is available for access by the user through the application executing on the portable device.

If it is determined that the sedentary collection interval is not complete, the example process 400 remains at decision block 416 until it is determined that the sedentary collection interval is complete. Upon determination that the sedentary collection interval is complete, the one or more processors of the wearable device are transitioned to the active state so that the collected sensor data can be processed by the one or more processors to produce processed data, as in 422.

Returning to decision block 414, if it is determined that the user application access pattern is known, a determination is made as to whether a defined time remains before an anticipated application access by the user, as in 418. The defined time may be any determined amount of time that is necessary to process and transmit collected and stored data from the buffer of the wearable device to the portable device so that information representative of the sensor data is available to the user when the user accesses the application to view the information. For example, the defined time may be thirty seconds, one minute, two minutes, etc. In some implementations, the defined time may be based on a confidence in the anticipated access time determined based on the user application access pattern and/or based on an expected wireless connection probability (discussed below). For example, a confidence of the accuracy of the anticipated application access time may be determined based on a confidence level of the determined sedentary state user application access pattern. If the user is very routine, based on prior application accesses, as to when the user accesses the application during a sedentary state and/or the frequency with which the user accesses an application during a sedentary state, a high confidence value may be determined for the anticipated application access time. In comparison, if the user is highly variable as to when and/or the frequency with which the user accesses the application during a sedentary state, a low confidence value for the anticipated application access time may be determined.

If it is determined that a defined time remains before an anticipated access, a determination is made as to whether a buffer usage threshold has been reached, as in 420. As discussed above, a buffer usage threshold may be a percentage of the buffer size, an amount of the buffer size, and may vary based on, for example, an expected wireless connection ability, discussed further below, based on user preference, based on time until an anticipated application access during the sedentary state, etc. If it is determined that the buffer usage threshold has been satisfied, the one or more processors of the wearable device are transitioned to the active state to process the sensor data that has been collected and stored in the buffer, as in 422. If it is determined that the buffer usage threshold has not been satisfied, the example process 400 returns to decision block 418 and continues.

Returning to decision block 418, if it is determined that a defined time before the anticipated application access does not remain, the one or more processors of the wearable device are transitioned to the active state to process the sensor data that has been collected and stored in the buffer, as in 422.

A determination may also be made as to whether some or all of the sensor data is to be aggregated, as in 424. If it is determined that some or all of the sensor data is to be aggregated, for the sensor data that is to be aggregated, the example aggregate sensor data process 600, discussed below with respect to FIG. 6, is performed, as in 600. If it is determined that the sensor data is not to be aggregated, or that a portion of the sensor data is not to be aggregated, the sensor data that was collected during the collection interval during the sedentary state and stored in the buffer that is not to be aggregated is processed by the processor to produce processed data, as in 426.

In addition, the wireless transmitter is also transitioned back to the active state, as in 427, and the wireless connection between the wearable device and the portable device is re-established (or a new wireless connection is established), as in 428. Upon establishment of the wireless connection between the wearable device and the portable device associated with the user, the processed sensor data and/or the aggregated sensor data, returned from example process 600, is sent from the wearable device, via the wireless connection, to the portable device, as in 428. As discussed above, in some implementations, the processor may periodically transition to the active state and process the collected sensor data without transitioning the wireless transmitter to the active state and wirelessly transmitting the processed data. For example, in some implementations, the processor may continue to cycle between a low power state and an active state to process sensor data and the processed data stored in the buffer. At a different interval, it may be determined that the wireless transmitter is to be activated and the processed data wirelessly transmitted from the wearable device.

Finally, the example process 400 returns to block 402 and continues.

FIG. 5 is an example user active state process 500, in accordance with described implementations.

The example process 500 begins in response to a determination that a user is in an active state and may itself continually or periodically confirm, based at least in part on the sensor data, that the user is in the active state, as in 502. If it is determined that the user is not in the active state, the example process 500 returns to the example process 200 with an indication that the user is not in an active state, as in 504.

However, if it is determined that the user is in an active state, sensor data is collected and stored in the buffer of a memory of the wearable device, as in 506. In comparison to the sleep state and/or the sedentary state, the buffer size of the memory may not be increased during an active state as the collected sensor data may be processed and/or transmitted from the wearable device to the portable device more frequently, so that information representative of the sensor data is accessible to the user when the user accesses an application on the portable device. Alternatively, in some implementations, if it is determined that the user does not access the application during the active state (e.g., the user is swimming), the buffer size may be increased so that additional sensor data may be stored and the frequency of processing/transmission of the sensor data can be reduced, thereby conserving battery power during the active state.

A determination may also be made as to whether an active state user application access pattern is known for the user, as in 508. An active state user application access pattern may be a pattern at which the user generally or predictably accesses, during an active state, an application executing on the mobile device to view information representative of sensor data collected by sensors of the wearable device during the active state. In some implementations, the active state user application access pattern may be determined by a machine learning model that uses prior user application access patterns, locations of the user during active states and/or application access, duration of application accesses, duration of active states, etc., to predict an active state user application access pattern.

If it is determined that the active state user application access pattern is not known for the user, a determination is made as to whether an active collection interval is complete, as in 509. An active collection interval may be a defined interval of time during the active state in which sensor data is collected and stored in the buffer of the wearable device before processing and/or transmitting to the portable device. A processing/transmission point may occur upon completion of each defined active collection interval so that the data stored in the buffer during the immediately prior active collection interval can be processed and/or transmitted from the wearable device to the portable device to free up buffer usage and so the information representative of the collected sensor data is available for access by the user through the application executing on the portable device. In some implementations, the duration of the active collection interval may be shorter than the sedentary collection interval discussed above.

If it is determined that the active collection interval is not complete, the example process 500 remains at decision block 509 until it is determined that the active collection interval is complete. Upon determination that the active collection interval is complete, the collected sensor data is processed by the one or more processors to produce processed data and/or transmitted from the wearable device to the portable device so that information representative of the sensor data is available to the user through the application executing on the portable device, as in 510.

Returning to decision block 508, if it is determined that the user application access pattern is known, a determination is made as to whether a defined time remains before an anticipated application access by the user, as in 512. The defined time may be any determined amount of time that is necessary to process and transmit collected and stored data from the buffer of the wearable device to the portable device so that the information representative of the sensor data is available to the user when the user accesses the application to view the information. For example, the defined time may be thirty seconds, one minute, two minutes, etc. In some implementations, the defined time may be based on a confidence in the anticipated access time determined based on the user application access pattern and/or based on an expected wireless connection probability (discussed below). For example, a confidence of the accuracy of the anticipated application access time may be determined based on a confidence level of the determined active state user application access pattern. If the user is very routine, based on prior application accesses, as to when the user accesses the application during an active state and/or the frequency with which the user accesses an application during an active state, a high confidence value may be determined for the anticipated application access time. In comparison, if the user is highly variable as to when and/or the frequency with which the user accesses the application during an active state, a low confidence value for the application access time may be determined.

If it is determined that a defined time remains before an anticipated access, a determination is made as to whether a buffer usage threshold has been reached, as in 514. As discussed above, a buffer usage threshold may be a percentage of the buffer size, an amount of the buffer size, and may vary based on, for example, an expected wireless connection ability, discussed further below, based on user preference, based on time until an anticipated application access during the active state, etc. If it is determined that the buffer usage threshold has been satisfied, the collected and stored sensor data is processed and/or sent from the wearable device to the portable device, as in 510. If it is determined that the buffer usage threshold has not been satisfied, the example process 500 returns to decision block 512 and continues.

Returning to decision block 512, if it is determined that a defined time before the anticipated application access does not remain, the collected and stored sensor data is processed and/or sent from the wearable device to the portable device, as in 510.

As illustrated in the differences between the example processes 300 (FIGS. 3A-3B), 400 (FIGS. 4A-4B), and 500 (FIG. 5), during an active mode, the components of the wearable device may be maintained in the active state, sensor data collected at a normal frequency, and sensor data regularly processed and sent wirelessly from the wearable device to the portable device so that information representative of the sensor data is available to the user when the user accesses the application executing on the wearable device. In addition, by sampling at a normal frequency, more fine grain data, which may be relevant during an active state, is processed to produce the information for the user.

FIG. 6 is an aggregate sensor data process 600, in accordance with described implementations. The example process 600, which may be performed when it is determined during one of the other example processes, such as example process 300 (FIGS. 3A-3B) or 400 (FIGS. 4A-4B), that some or all of the collected sensor data is to be aggregated.

The example process 600 begins by comparing sensor data that is available for aggregation and collected over a defined period of time (e.g., collection interval) that falls within a defined comparison capture window, as in 602. The defined comparison capture window may be an adjustable window that begins by comparing a portion of the sensor data that was collected during a collection interval to determine if the sensor data varies more than a defined aggregation range. For example, if sensor data that is available for aggregation is collected during a ten minute collection interval, the defined comparison window may be 5% of that collection interval (e.g., 15 seconds). In other examples, the defined capture window may be larger or smaller. For sensor data falling within the defined capture window, the example process 600 may compare the sensor data to determine if the compared sensor data is within a defined aggregation range. The defined aggregation range may be any measure to determine if the compared data changes more than a non-material amount such that it should not be aggregated. For example, the aggregation range may be a defined window around an average or median of the compared sensor data (e.g., ±2%), more than a standard deviation from other compared sensor data, etc.

Based on the compared sensor data, a determination may be made as to whether the compared sensor data is all within the aggregation range, as in 604. If it is determined that the compared data is within the aggregation range, a determination is made as to whether the comparison capture window is to be expanded, as in 606. If it is determined that the comparison capture window is to be expanded, the comparison capture window is expanded to include additional sensor data that is available for aggregation, as in 614.

Returning to decision block 604, if it is determined that the compared sensor data is not within the aggregation range, a determination is made as to whether the comparison capture window was previously expanded as part of the example process 600, as in 608. If the comparison capture window was previously expanded, then a prior comparison of sensor data for the prior comparison capture window was determined to be within the aggregation range.

If it is determined that the comparison capture window was previously expanded, the data within the prior comparison capture window is aggregated, as in 612. As discussed above, data may be aggregated to reduce the overall amount of data that is transmitted from the wearable device to the portable device. For example, a mean or median sensor data value may be selected as representative of the aggregated sensor data and just that sensor data value, and an indication of the time period represented by the sensor data value, sent from the wearable device to the portable device as representative of the aggregated sensor data. By only transmitting the sensor data value rather than all of the sensor data that was aggregated, the total amount of data transmitted is dramatically reduced, thereby reducing the connection duration and conserving battery power of the battery of the wearable device. In some implementations, the sensor data that was aggregated may be maintained in a memory of the wearable device and transmitted from the wearable device to the portable device when it is determined that the wearable device is connected to a power source (i.e., during a battery recharge) and battery conservation is not an issue.

If it is determined at decision block 608 that the comparison capture window was not previously expanded as part of the example process 600, the example process 600 returns an indication that the data is not to be aggregated, as in 610.

Returning to decision block 606, if it is determined that the comparison capture window is not to be expanded, for example that comparison capture window is the same size as the collection interval such that all sensor data available for aggregation is included in the comparison capture window, the sensor data included in the comparison capture window is aggregated, as in 616. As discussed above, data may be aggregated to reduce the overall amount of data that is transmitted from the wearable device to the portable device. For example, a mean or median sensor data value may be selected as representative of the aggregated sensor data and just that sensor data value, and an indication of the time period represented by the sensor data value, sent from the wearable device to the portable device as representative of the aggregated sensor data. By only transmitting the sensor data value rather than all of the sensor data that was aggregated, the total amount of data transmitted is dramatically reduced, thereby reducing the connection duration and conserving battery power of the battery of the wearable device. In some implementations, the sensor data that was aggregated may be maintained in a memory of the wearable device and transmitted from the wearable device to the portable device when it is determined that the wearable device is connected to a power source (i.e., during a battery recharge) and battery conservation is not an issue.

After aggregating the sensor data at blocks 612 or 616, the aggregated sensor data value representative of the aggregated data is returned as representative of the aggregated sensor data, as in 618.

Figure 7:
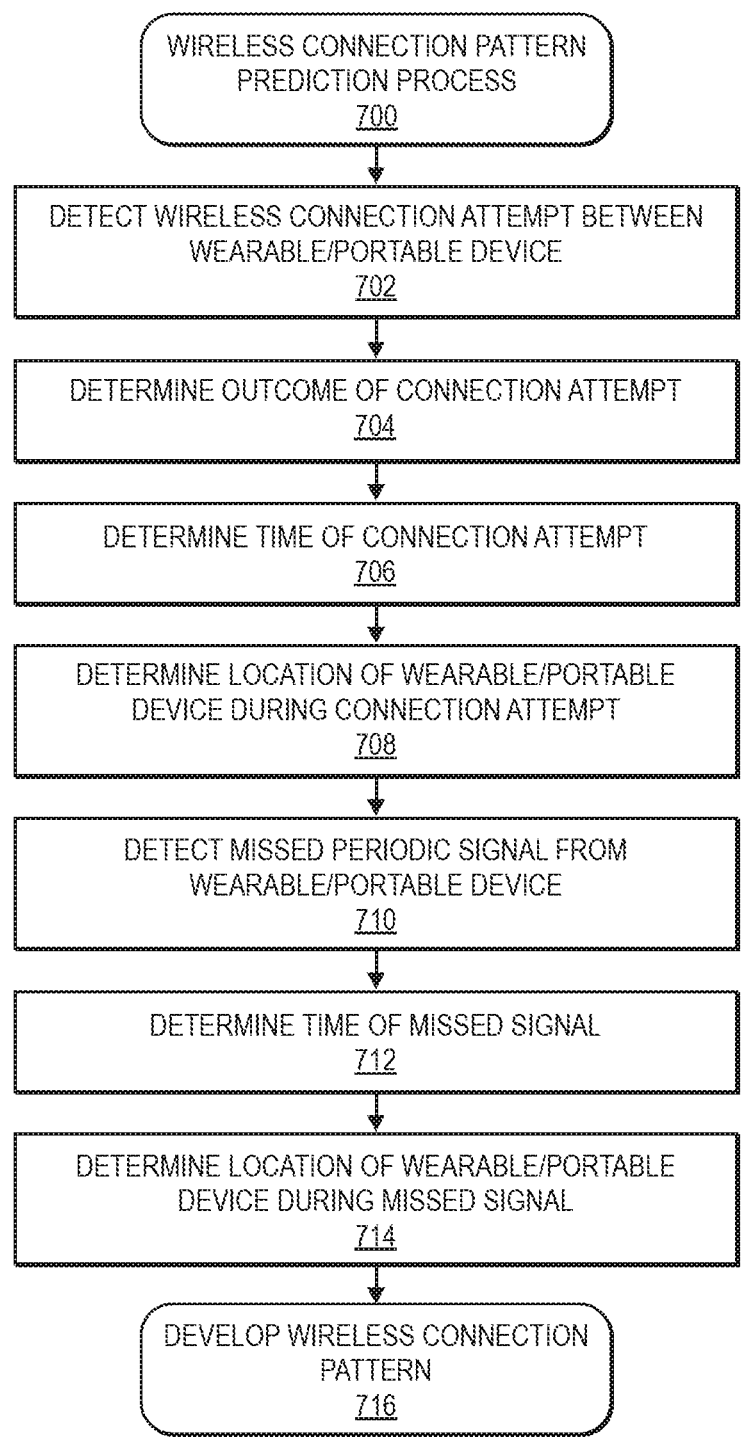
FIG. 7 is an example wireless connection pattern prediction process, in accordance with described implementations.

FIG. 7 is an example wireless connection pattern prediction process 700, in accordance with described implementations. The example process 700 may be performed on the wearable device and/or the portable device and the results provided to the wearable device to determine a wireless connection probability during other example processes discussed herein.

The example process 700 begins by detecting a wireless connection attempt between the wearable device and the portable device, as in 702. A wireless connection attempt may be any attempt between the wearable device and the portable device to exchange data. For example, the wireless connection attempt may include a connection negotiation between the wearable device and the portable device to establish a wireless connection, a request to transfer data from the wearable device to the portable device, a request to transfer data from the portable device, etc.

For the connection attempt, a determination is made as to the outcome of the connection attempt, as in 704. A connection attempt is considered successful if the purpose of the connection attempt is completed. For example, if the connection attempt is to transfer data from the wearable device to the portable device, the connection attempt is successful if the transfer of the data is completed, and optionally verified. A connection attempt is considered unsuccessful if the purpose of the connection is not successfully completed, or if multiple connection attempts are required to complete the purpose of the connection attempt.

In addition to determining the connection attempt and the outcome of the connection attempt, one or more of the time of the connection attempt may be determined, as in 706, and/or the location of the wearable device and/or the portable device during the connection attempt determined may be determined, as in 708. In other implementations, other information may also be determined. For example, the signal strength between the wearable device and the portable device, the duration of the connection, the activity state of the user during the connection attempt, etc., may also be determined with respect to a detected connection attempt.

The example process may also monitor for missed periodic signals that are exchanged between the wearable device and the portable device that are used to maintain an established wireless connection, as in 710. For example, many wireless protocols, such as BLUETOOTH, periodically exchange or send signals, often referred to as heartbeats, between devices to confirm to the receiving device that the other, transmitting device, is still within range and that the wireless connection/channel is to be maintained between the devices. A missed signal or set of missed signals may be indicative of a poor wireless connection between the devices and/or that the devices are no longer in range of one another such that the wireless connection is not available.

For each missed signal or group of missed signals, one or more of the time of the missed signal may be determined, as in 712, and/or the location of the wearable device and/or the portable device during the missed signal may be determined, as in 714. In other implementations, other information may also be determined. For example, the number of missed signals in a group of missed signals may be determined, the activity state of the user during the missed signal(s), etc., may also be determined with respect to a missed signal or group of missed signals.

Based on the information collected by the example process 700 for connection attempts and/or missed periodic signals, over a period of time, a wireless connection pattern is developed that is representative of wireless connection probabilities between the wearable device and the portable device, as in 716. For example, the information collected by the example process may be provided to one or more machine learning models that process the information and determine wireless connection probabilities based on one or more of the time of day, day of the week, location of the portable device, location of the wearable device, the activity state of the user, etc. For example, each time a connection attempt may be performed or skipped by one or more of the example processes discussed herein, a wireless connection probability for the connection may be determined based on the wireless connection pattern developed as a result of the example process 700.

In some implementations, the example process 700 may periodically or continually be performed by one or both of the wearable device and the portable device and the wireless connection pattern determined by the example process 700 updated and refined as additional connection attempts and missed signals are detected and processed.

Figure 8:
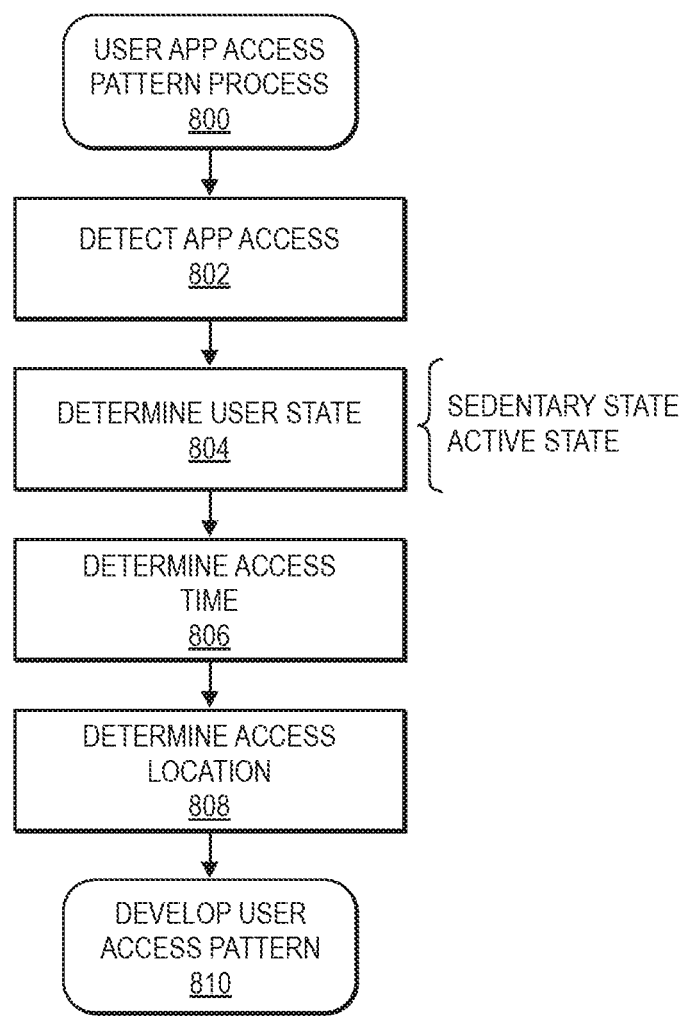
FIG. 8 is an example user application access pattern prediction process, in accordance with described implementations.

FIG. 8 is an example user application access pattern prediction process 800, in accordance with described implementations. The example process 800 may be performed on the portable device that is associated with the user wearing the wearable device.

The example process 800 begins by detecting an application access to the application executing on the portable device that provides information representative of the sensor data collected by the wearable device to the user, as in 802. In some implementations, the example process 800 may also monitor the frequency with which the user accesses the portable device, regardless of whether the user accesses the application.

For each access by the user to the application executing on the portable device, a user state of the user during the access is determined, as in 804. For example, the example process 800 may determine a time of the access, as in 806, and determine that state of the user at that time based on sensor data/processed data received from the wearable device that corresponds with the time of the access of the application by the user. In the above examples, the user state would be either a sedentary state or an active state (assuming the user would not access the application on the portable device during a sleep state). In other examples that include fewer or additional states, additional or fewer states of the user may be determined.

In addition to determining the time of the access and the state of the user during the access, the example process may also determine the location of the portable device and/or the wearable device during the time of the access, as in 808. In other implementations, additional information may be determined that corresponds to each application access. For example, the content accessed by the user through the application, the duration of application access, etc., may also be determined.

Based on the information determined by the example process 800 for each of a plurality of application accesses during a period of time, a user access pattern is developed that is representative of an application access pattern by the user, as in 810. For example, the information collected by the example process 800 may be provided to one or more machine learning models that process the data and determine user access patterns based on one or more of the time of day, day of week, location of the portable device, location of the wearable device, the activity state of the user, duration of application access, information accessed through the application, etc. For example, each time a determination is made as to whether data needs to be transmitted from the wearable device to the portable device and/or each time a determination is made as to whether a user is going to access the application executing on the portable device, a user access probability may be determined that is indicative of a confidence as to whether the user is about to access the application executing on the portable device.

In some implementations, the example process 800 may periodically or continually be performed and the user application access pattern determined by the example process 800 updated and refined as additional application accesses by the user occur.

Figure 9:
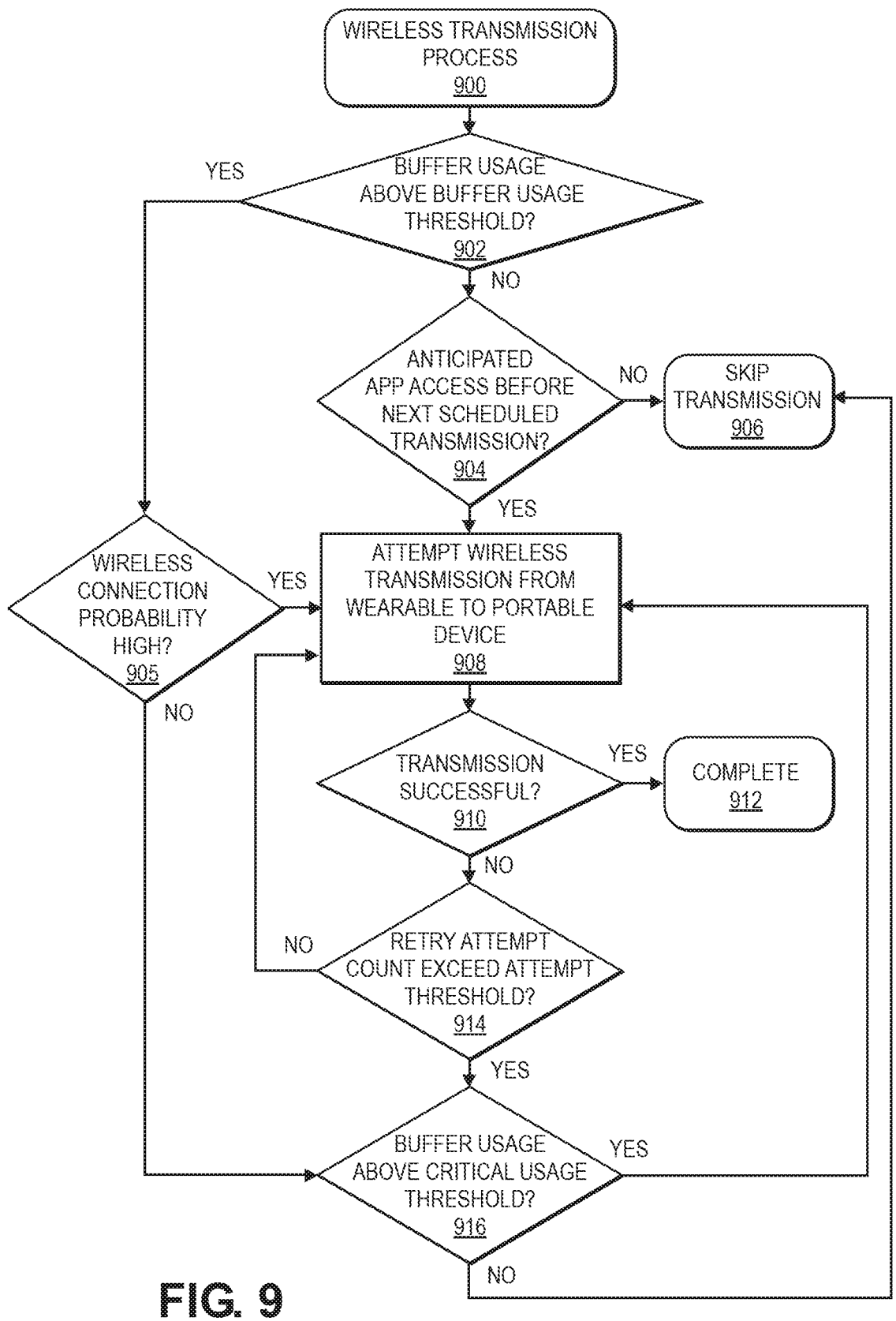
FIG. 9 is an example wireless transmission process, in accordance with described implementations.

FIG. 9 is an example wireless transmission process 900, in accordance with described implementations.

The example process 900 may be performed periodically by the wearable device in parallel with one or more of the example processes discussed herein and/or performed as part of the example processes discussed herein when a wireless transmission is to be initiated by one of the example processes.

The example process 900 begins by determining if a usage of a buffer in a memory of the wearable device is above a buffer usage threshold, as in 902. As discussed above, a buffer of varying size depending on the determined state of the user may be allocated in memory and collected sensor data stored in the buffer until it is processed and/or transmitted from the wearable device to the portable device.

If it is determined that the buffer usage is above the buffer usage threshold, a determination is made as to whether the wireless connection probability between the wearable device and the portable device is high, as in 905. As discussed above, the wireless connection probability may be determined, for example, based on the developed wireless connection pattern, determined from example process 700 (FIG. 7) and/or based on the current location of the wearable device/portable device, time of day, etc. If it is determined that the wireless connection probability is high, the example process 900 proceeds to decision block 916, discussed further below. If it is determined that the wireless connection probability is not high, the example process 900 proceeds to block 908, discussed below.

Returning to decision block 902, if it is determined that the buffer usage does not exceed the buffer usage threshold, a determination is made as to whether an application access is predicted to occur before a next scheduled transmission of sensor data from the wearable device to the portable device, as in 904. The determination may be made based on, for example, the application access pattern determined for the user by the example process 800 (FIG. 8) and discussed above. For example, the example process 900 may utilize the determined application access pattern for the user, the current state of the user, the time since last application access, etc., to determine a next anticipated application access by the user.

Likewise, as discussed above, wireless transmissions may be performed between the wearable device and the portable device at intervals, which may be determined based on the state of the user.

If it is determined that the next anticipated application access by the user is not before a next scheduled transmission of sensor data from the wearable device to the portable device, the transmission of the data may be skipped, as in 906. If it is determined that the next anticipated application access by the user may occur before the next wireless transmission, a wireless transmission of the collected and stored sensor data, or processed sensor data, is attempted between the wearable device and the portable device, as in 908.

For the attempted wireless transmission, a determination may be made as to whether the transmission was successful, as in 910. If the wireless transmission was successful, the example process 910 completes, as in 912. However, if it is determined that the attempted transmission was not successful, a determination may be made as to whether a retry attempt count exceeds an attempt threshold, as in 914. The retry attempt count may be incremented for each successive failed transmission attempt for transmission of the sensor data by the example process 900. The attempt count may be any defined amount and may vary based on, for example, the state of the user, the confidence of the likelihood of the anticipated next user application access attempt, the amount of buffer available beyond the buffer usage threshold, the last time since data was successfully sent from the wearable device to the portable device, the current wireless connection probability, etc. For example, if the current wireless connection probability is high, as determined from the wireless connection pattern determined by the example process 700, the attempt threshold may be higher. In comparison, if the wireless connection probability is low, the attempt threshold may be lower. In some implementations, the attempt threshold may be zero.

If it is determined that the retry attempt count does not exceed the attempt threshold, the example process returns to block 908 and again attempts to transmit the sensor data. If it is determined that the retry attempt count exceeds the threshold, a determination is made as to whether the buffer usage is above a critical usage threshold, as in 916. The critical usage threshold may be any amount of the buffer usage and may vary for different users based on, for example, the time since last transmission, etc. In some implementations, the critical usage threshold may be a defined amount above the buffer usage threshold discussed above. The critical usage threshold may be used to shift from battery conservation to data conservation in that, if the critical usage threshold has been reached, as discussed, the wireless connection may be retried in an effort to establish the connection and transfer sensor data before the buffer is full and some of the data must be purged from the buffer or not stored in the buffer and thus discarded or lost.

If it is determined that the buffer usage of the buffer is above the critical usage threshold, the example process 900 returns to block 908 and continues. If it is determined that the buffer usage does not exceed the critical usage threshold, the example process 900 returns to block 906 and the attempted transmission is skipped.

Figure 10:
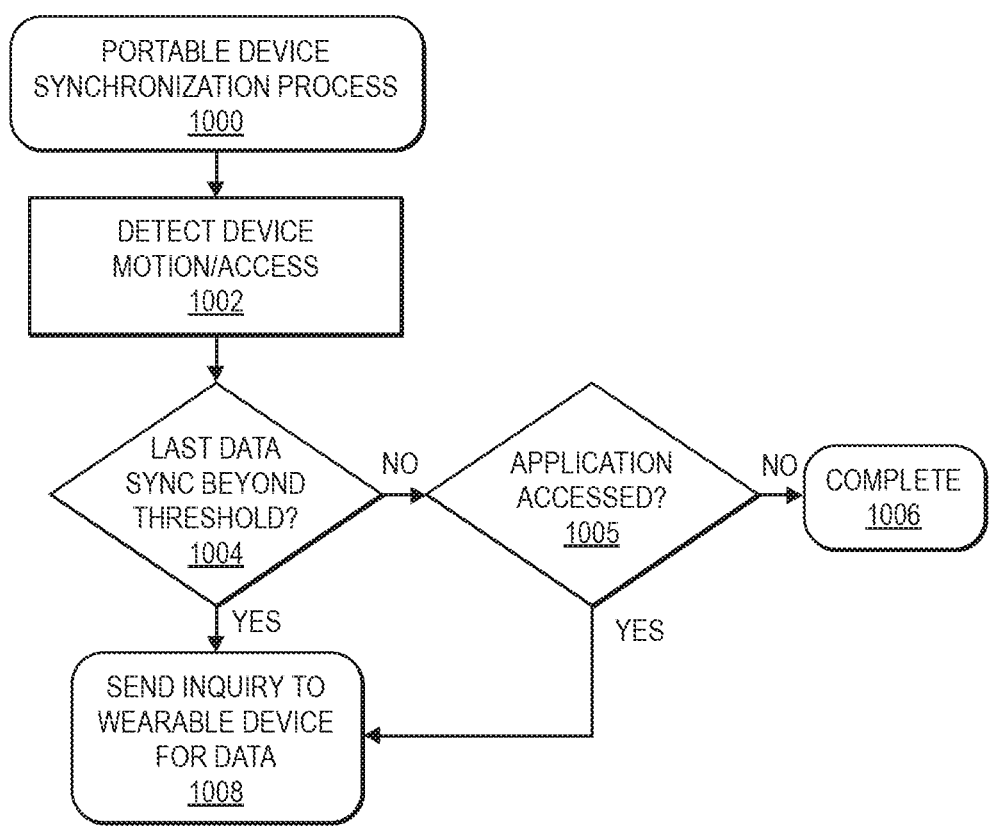
FIG. 10 is an example portable device synchronization process, in accordance with described implementations.

FIG. 10 is an example portable device synchronization process 1000, in accordance with described implementations.

The example process 1000 may be performed on the portable device and used in an effort to transfer previously not transferred sensor data from the wearable device to the portable device so that information representative of the most current sensor data is available to the user when the user accesses the application executing on the portable device.

The example process 1000 begins upon detection of a motion and/or access of the portable device (e.g., a screen unlock event), as in 1002. For example, in some implementations, the application executing on the portable device may receive event notifications from the portable device indicating when the portable device is moved (e.g., picked up by the user) and/or when the user accesses the portable device.

In response to determining a motion or access of the portable device, a determination is made as to whether a last synchronization of sensor data/processed data from the wearable device was beyond a threshold, as in 1004. The threshold may be different for different users, different times of day, etc. In some implementations, the threshold may be five minutes. In such an example, if the last receipt or synchronization of data from the wearable device was more than five minutes prior to the detected device movement and/or device access, it may be determined that the last synchronization is beyond the threshold.

If it is determined that the last synchronization was not beyond the last threshold, a determination is made as to whether the user actually accesses the application executing on the wearable device, as in 1005. If it is determined that the user does not access the application, the example process 1000 completes, as in 1006.

If it is determined at decision block 1004 that the last synchronization of sensor data/processed data is beyond the threshold, or it is determined at decision block 1005 that the user has accessed the application executing on the portable device, an inquiry is sent from the portable device to the wearable device as to whether sensor data is stored on the wearable device that has not been provided to the application executing on the portable device, as in 1008. A variety of protocols may be used to determine if sensor data is stored on the wearable device that has not been sent to the application executing on the portable device. For example, the application may send from the portable device a request as to whether the wearable device has any data to provide to the portable device. The wearable device, in response may provide an indication that either data is available or not available. If data is available, in response to the indication, the portable device may establish a wireless connection with the wearable device and receive the data. In another example, rather than sending the request and receiving an indication as to whether data is available, the portable device may initially establish the wireless connection and any available data provided from the wearable device to the portable device.

Figure 11:
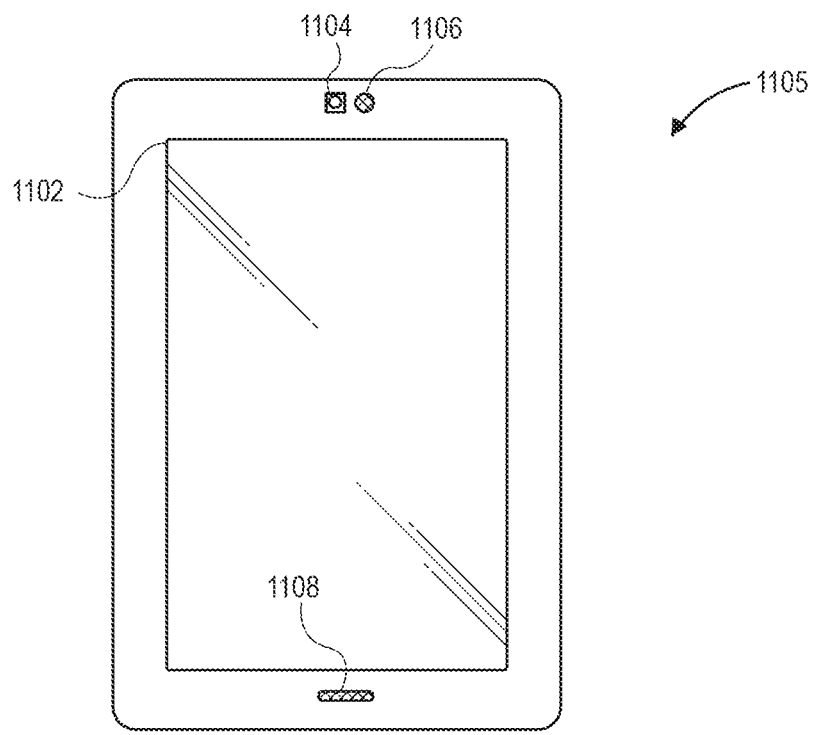
FIG. 11 illustrates an example portable device that can be used in accordance with various implementations.

FIG. 11 illustrates an example portable device 1105 that can be used in accordance with various implementations described herein. In this example, the portable device 1105 includes a display 1102 and optionally at least one input component 1104, such as a camera, on a same side of the device as the display 1102. The portable device 1105 may also include an audio transducer, such as a speaker 1106, and optionally a microphone 1108. Generally, the portable device 1105 may have any form of input/output components that allow a user to interact with the portable device 1105. For example, the various input components for enabling user interaction with the device may include a touch-based display 1102 (e.g., resistive, capacitive, Interpolating Force-Sensitive Resistance (IFSR)), camera (for gesture tracking, etc.), microphone, global positioning system (GPS), compass or any combination thereof. Various other input components and combinations of input components can be used as well within the scope of the various implementations as should be apparent in light of the teachings and suggestions contained herein.

Figure 12:
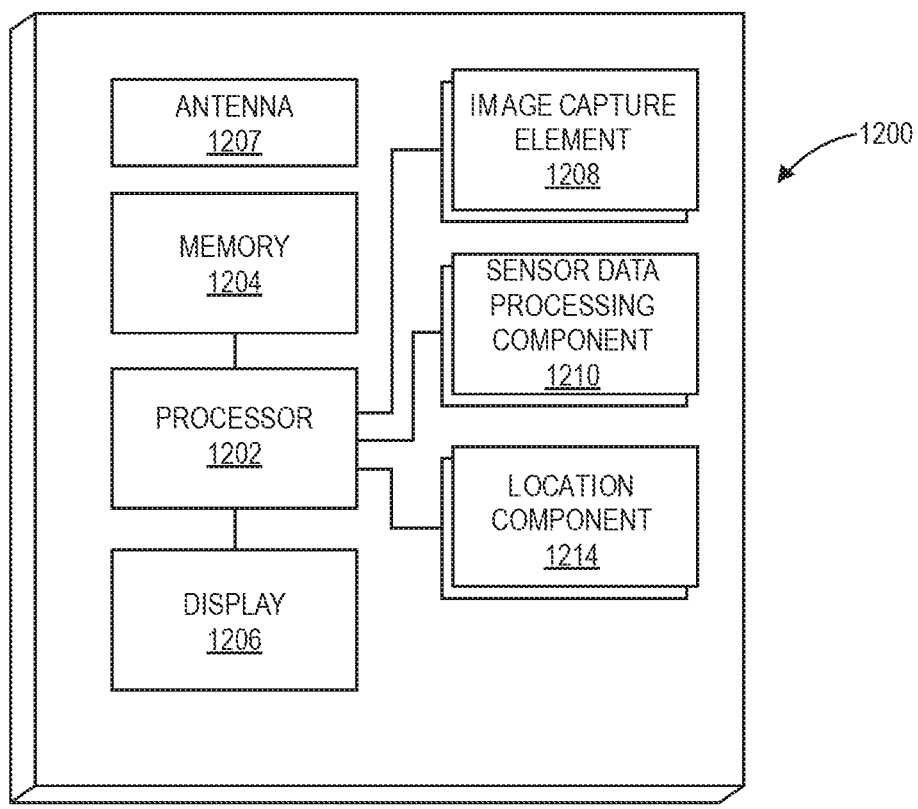
FIG. 12 illustrates an example configuration of components of a portable device, such as that illustrated in FIG. 11.

In order to provide the various functionality described herein, FIG. 12 illustrates an example set of basic components 1200 of a portable device 1105, such as the portable device 1105 described with respect to FIG. 11 and discussed herein. In this example, the device includes at least one central processor 1202 for executing instructions that can be stored in at least one memory device or element 1204. As would be apparent to one of ordinary skill in the art, the device can include many types of memory, data storage or computer-readable storage media, such as a first data storage for program instructions for execution by the processor 1202. Removable storage memory can be available for sharing information with other devices, etc. The device typically will include some type of display 1206, such as a touch-based display, organic light emitting diode (OLED) or liquid crystal display (LCD).

The device in many implementations will include at least one image capture element 1208, such as one or more cameras that are able to image objects in the vicinity of the device. An image capture element can include, or be based at least in part upon, any appropriate technology, such as a CCD or CMOS image capture element having a determined resolution, focal range, viewable area, and capture rate. The device can include at least one sensor data processing component 1210 operable to process sensor data received, for example, from a wearable device, such as the wearable device 101 discussed with respect to FIG. 1.

The device also can include at least one location component 1214, such as GPS, NFC location tracking or Wi-Fi location monitoring. Location information obtained by the location component 1214 may be used with the various implementations discussed herein to identify the location of the portable device, the location of the wearable device, and/or the location of the user.

The portable device may also include one or more antennas 1207 that enable wireless communication between the portable device and the wearable device, as discussed herein. Any form of wireless communication may be used to enable communication between the portable device and the wearable device, including, but not limited to, Wi-Fi, Bluetooth, NFC, etc. In addition, the one or more antennas 1207 may also provide wireless communication between the portable device and one or more other devices that are remote from the portable device and the wearable device.

The example portable device may also include at least one additional input device able to receive conventional input from a user. This conventional input can include, for example, a push button, touch pad, touch-based display, wheel, joystick, keyboard, mouse, trackball, keypad or any other such device or element whereby a user can input a command to the device. These I/O devices could be connected by a wireless, infrared, Bluetooth, or other link as well in some implementations. In some implementations, however, such a device might not include any buttons at all and might be controlled only through touch (e.g., touch-based display), audio (e.g., spoken) commands, or a combination thereof.

The above aspects of the present disclosure are meant to be illustrative. They were chosen to explain the principles and application of the disclosure and are not intended to be exhaustive or to limit the disclosure. Many modifications and variations of the disclosed aspects may be apparent to those of skill in the art. Persons having ordinary skill in the field of computers, communications, etc., should recognize that components and process steps described herein may be interchangeable with other components or steps, or combinations of components or steps, and still achieve the benefits and advantages of the present disclosure. Moreover, it should be apparent to one skilled in the art that the disclosure may be practiced without some or all of the specific details and steps disclosed herein. Moreover, with respect to the one or more methods or processes of the present disclosure described herein, including but not limited to the flow charts shown in FIGS. 2 through 10, orders in which such methods or processes are presented are not intended to be construed as any limitation on the claimed inventions, and any number of the method or process steps or boxes described herein can be combined in any order and/or in parallel to implement the methods or processes described herein, and/or omitted. Also, the drawings herein are not drawn to scale.

Aspects of the disclosed apparatus, method, and system may be implemented as a computer method or as an article of manufacture such as a memory device or non-transitory computer readable storage medium. The computer readable storage medium may be readable by a computer and may comprise instructions for causing a computer or other device to perform processes described in the present disclosure. The computer readable storage media may be implemented by a volatile computer memory, non-volatile computer memory, hard drive, solid-state memory, flash drive, removable disk, and/or other media. In addition, components of one or more of the modules and engines may be implemented in firmware or hardware.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

Language of degree used herein, such as the terms "about," "approximately," "generally," "nearly" or "substantially," as used herein, represent a value, amount, or characteristic close to the stated value, amount, or characteristic that still performs a desired function or achieves a desired result. For example, the terms "about," "approximately," "generally," "nearly" or "substantially" may refer to an amount that is within less than 10% of, within less than 5% of, within less than 1% of, within less than 0.1% of, and within less than 0.01% of the stated amount.

Although the invention has been described and illustrated with respect to illustrative implementations thereof, the foregoing and various other additions and omissions may be made therein and thereto without departing from the spirit and scope of the present disclosure.

What is claimed is:

1. A wearable device apparatus, comprising:
   a battery;
   one or more processors powered by the battery;
   a wireless transmitter powered by the battery;
   a plurality of sensors powered by the battery; and
   a memory storing program instructions that, when executed by the one or more processors, cause the one or more processors to at least:
      establish a first wireless connection between the wireless transmitter of the wearable device apparatus and a portable device;
      collect, with each of the plurality of sensors, sensor data corresponding to a user wearing the wearable device apparatus;
      determine, based at least in part on at least a first portion of the sensor data, that the user is in a first state, wherein the first state is different than a sleep state;
      while the user is in the first state:
         store, in a buffer having a first buffer size in a memory of the wearable device apparatus and during a first interval duration that occurs between each of a first plurality of data transmission points, the sensor data;
         at each data transmission point:
            process, with the one or more processors, the sensor data stored in the buffer during the first interval duration immediately prior to the data transmission point to produce first processed data; and
            transmit, via the first wireless connection, the first processed data from the wearable device apparatus to the portable device such that the first processed data is available to the user through the portable device;
      determine, based at least in part on at least a second portion of the sensor data that is collected subsequent to the at least a first portion of the sensor data, that the user wearing the wearable device apparatus has transitioned from the first state to the sleep state;
      in response to determination that the user has transitioned to the sleep state:
         increase a buffer size of the buffer from the first buffer size to a second buffer size that is larger than the first buffer size;
         terminate the first wireless connection between the wearable device apparatus and the portable device;
         transition the one or more processors to a low power state;
         transition the wireless transmitter to the low power state;
         continue to collect, with each of the plurality of sensors, the sensor data; and
         store the sensor data in the buffer having the second buffer size;
      determine that a defined portion of a predicted sleep state duration of the sleep state has completed, wherein the defined portion is longer than the first interval duration;
      in response to determination that the defined portion of the predicted sleep state duration of the sleep state has completed, and prior to a completion of the sleep state:
         transition the one or more processors from the low power state to an active state;
         process, with the one or more processors, the sensor data stored in the buffer of the memory during the defined portion of the predicted sleep state duration to produce second processed data;
         transition the wireless transmitter from the low power state to the active state;

establish a second wireless connection between the wearable device apparatus and the portable device; and transmit, via the second wireless connection, the second processed data from the wearable device apparatus to the portable device such that the second processed data is available to the user when the user exits the sleep state and accesses the portable device.

2. The wearable device apparatus of claim 1, wherein the program instructions, when executed by the one or more processors further cause the one or more processors to at least:

determine, while the user is in the sleep state and before the defined portion of the predicted sleep state duration of the sleep state has completed, that a buffer usage threshold corresponding to a percentage of the second buffer size being filled has been satisfied;

in response to determination that the buffer usage threshold has been satisfied:
transition the one or more processors from the low power state to the active state;
process, with the one or more processors, the sensor data stored in the buffer of the memory during the sleep state to produce third processed data;
subsequent to processing the sensor data, transition the one or more processors to the low power state;
transition the wireless transmitter from the low power state to the active state;
establish a third wireless connection between the wearable device apparatus and the portable device;
transmit, via the third wireless connection, the third processed data from the wearable device apparatus to the portable device;
subsequent to transmission of the third processed data:
terminate the third wireless connection; and
transition the wireless transmitter to the low power state.

3. The wearable device apparatus of claim 1, wherein the program instructions that when executed by the one or more processors, further cause the one or more processors to at least:

determine, based at least in part on the sensor data, that a sleep state completion is approaching; and wherein in response to determination that the defined portion of the predicted sleep state duration of the sleep state has completed is further in response to determination that the defined portion of the predicted sleep state duration of the sleep state has completed or in response to determination that the sleep state completion is approaching.

4. The wearable device apparatus of claim 3, wherein determination that the sleep state completion is approaching is based at least in part on sensor data from at least one of a heartrate sensor, a blood pressure sensor, a movement sensor, or a temperature sensor.

5. The wearable device apparatus of claim 1, wherein the program instructions, when executed by the one or more processors, further cause the one or more processors to at least:

determine, based at least in part on a plurality of prior sleep state durations experienced by the user, the predicted sleep state duration.

6. A computer-implemented method, comprising:

determining, based at least in part on sensor data collected by a plurality of sensors of a wearable device worn by a user, that the user is in a first state;

in response to determining that the user is in the first state:
storing in a buffer of a memory, the buffer having a first buffer size, sensor data collected during each of a first plurality of intervals having a first interval duration; and
transmitting periodically and upon completion of each of the first plurality of intervals, the sensor data stored in the buffer during the first interval duration from the wearable device to a portable device associated with the user;

determining, based at least in part on the sensor data collected by the plurality of sensors, that the user has transitioned from the first state to a second state that is different than the first state;

in response to determining that the user has transitioned to the second state:
altering a buffer size of the buffer from the first buffer size to a second buffer size that is different than the first buffer size;
storing in the buffer having the second buffer size, sensor data collected during each of a second plurality of intervals having a second interval duration that is different than the first interval duration; and
transmitting periodically and upon completion of each of the second plurality of intervals, the sensor data stored in the buffer during the second interval duration from the wearable device to the portable device.

7. The computer-implemented method of claim 6, further comprising:

determining, based at least in part on the sensor data collected by the plurality of sensors, that the user has transitioned from the second state to a third state that is different than the first state and the second state;

in response to determining that the user has transitioned to the third state:
altering the buffer size of the buffer from the second buffer size to a third buffer size that is different than at least one of the first buffer size or the second buffer size; and
storing in the buffer having the third buffer size, sensor data collected during each of a third plurality of intervals having a third interval duration that is different than the first interval duration and the second interval duration; and
transmitting periodically and upon completion of each of the third plurality of intervals, the sensor data stored in the buffer during the third interval duration.

8. The computer-implemented method of claim 6, wherein the first state is at least one of an active state of the user, a sedentary state of the user, or a sleep state of the user.

9. The computer-implemented method of claim 8, further comprising:

aggregating at least a portion of the sensor data collected during at least one of the first interval durations and stored in the buffer having the first buffer size to produce aggregated sensor data; and wherein transmitting includes transmitting the aggregated sensor data without transmitting the at least a portion of the sensor data that was aggregated.

10. The computer-implemented method of claim 9, wherein aggregating the at least a portion of the sensor data includes:

determining that sensor data values of the at least a portion of the sensor data is within a defined range; and in response to determining that the sensor data values of the at least a portion of the sensor data is within the defined range, selecting, as the aggregated sensor data, a sensor data value as representative of the sensor data values of the at least a portion of the sensor data.

11. The computer-implemented method of claim 6, further comprising:
determining, based at least in part on a plurality of prior second state durations experienced by the user, a predicted second state duration; and
wherein the second interval duration is based at least in part on the predicted second state duration.

12. The computer-implemented method of claim 6, further comprising:
determining, prior to a completion of a second interval duration, that a sleep state completion is approaching; and
in response to determining that the sleep state completion is approaching, and prior to a sleep state completion, transmitting the sensor data stored in the buffer from the wearable device to the portable device.

13. The computer-implemented method of claim 12, wherein determination that the sleep state completion is approaching is based at least in part on sensor data from at least one of a heartrate sensor, a blood pressure sensor, a movement sensor, or a temperature sensor.

14. The computer-implemented method of claim 6, further comprising:
in response to determining that the user has transitioned to the second state, altering a processing frequency of at least some of the sensor data from a first processing frequency to a second processing frequency, wherein the second processing frequency is different than the first processing frequency.

15. The computer-implemented method of claim 6, further comprising:
in response to determining that the user has transitioned to the second state:
terminating a wireless connection between the wearable device and the portable device; and
transitioning a wireless transmitter of the wearable device from an active state to a low power state.

16. A wearable device apparatus, comprising:
a power source;
one or more processors powered by the power source;
a sensor powered by the power source;
a wireless transmitter powered by the power source; and
a memory storing program instructions that when executed by the one or more processors cause the one or more processors to at least:
maintain, while a user wearing the wearable device apparatus is in a first state, at least the wireless transmitter in a low power state;
store, in a buffer of a memory of the wearable device apparatus, sensor data collected by the sensor while the user is in the first state;
determine that at least one of a buffer usage threshold has been satisfied or that a first state completion of the first state is approaching; and
in response to determination that at least one of the buffer usage threshold has been satisfied or that the first state completion is approaching, and before a completion of the first state:
transition the wireless transmitter from the low power state to an active state; and
initiate, with the wireless transmitter, a transmission of the sensor data stored in the buffer from the wearable device apparatus to a user device so that information corresponding to the sensor data is available to the user after the completion of the first state.

17. The wearable device apparatus of claim 16, wherein the first state is at least one of a sleep state or an active state.

18. The wearable device apparatus of claim 16, wherein a determination that a first state completion is approaching is based at least in part on sensor data from at least one of a heartrate sensor, a blood pressure sensor, a movement sensor, or a temperature sensor.

19. The wearable device apparatus of claim 16, wherein the program instructions that when executed by the one or more processors further cause the one or more processors to at least:
determine that the user has transitioned from the first state to a second state that is different than the first state; and
in response to determination that the user has transitioned from the first state to the second state, adjust a buffer size of the buffer from a first buffer size corresponding to the first state and a second buffer size corresponding to the second state, wherein the first buffer size is different than the second buffer size.

20. The wearable device apparatus of claim 16, wherein the program instructions that when executed by the one or more processors further cause the one or more processors to at least:
determine that a defined time before a predicted application access by the user during the first state has been reached; and
in response to determination that the defined time before the predicted application access by the user during the first state has been reached, transmit the sensor data stored in the buffer from the wearable device apparatus.

21. The wearable device apparatus of claim 16, wherein the program instructions that when executed by the one or more processors further cause the one or more processors to at least:
determine that the transmission failed;
in response to determination that the transmission failed, determine that at least one of a transmission count or a buffer memory threshold has been exceeded; and
in response to determination that at least one of the transmission count or the buffer memory threshold has been exceeded, retry the transmission.

22. The wearable device apparatus of claim 16, wherein the wearable device apparatus is at least one of a wristband, a necklace, a headphone, a ring, a watch, an earring, a headband, a glasses, a clothing, or an on-skin apparatus.

* * * * *